(12) United States Patent
Kato et al.

(10) Patent No.: US 7,831,394 B2
(45) Date of Patent: *Nov. 9, 2010

(54) INFORMATION PROCESSING SYSTEM USING NUCLEOTIDE SEQUENCE-RELATED INFORMATION

(75) Inventors: Takamasa Kato, Tokorozawa (JP); Takeo Morimoto, Koshigaya (JP)

(73) Assignee: Hitachi, Ltd., Tokyo (JP)

( * ) Notice: Subject to any disclaimer, the term of this patent is extended or adjusted under 35 U.S.C. 154(b) by 80 days.

This patent is subject to a terminal disclaimer.

(21) Appl. No.: 12/003,012

(22) Filed: Dec. 19, 2007

(65) Prior Publication Data
US 2008/0154516 A1 Jun. 26, 2008

Related U.S. Application Data

(63) Continuation of application No. 10/534,979, filed on May 16, 2005, now Pat. No. 7,337,071.

(30) Foreign Application Priority Data
Nov. 18, 2002 (JP) .............................. 2002-334161

(51) Int. Cl.
*G01N 7/00* (2006.01)
(52) U.S. Cl. .............................. 702/19; 702/20; 703/11; 703/12; 703/13; 707/102; 536/23.1; 435/6
(58) Field of Classification Search ........................ None
See application file for complete search history.

(56) References Cited

U.S. PATENT DOCUMENTS

| | | | |
|---|---|---|---|
| 6,675,166 | B2 | 1/2004 | Bova |
| 2001/0037340 | A1 | 11/2001 | Hawkins et al. |
| 2002/0002474 | A1 | 1/2002 | Michelson et al. |
| 2002/0010552 | A1 | 1/2002 | Rienhoff, Jr. et al. |
| 2002/0019746 | A1 | 2/2002 | Rienhoff et al. |
| 2002/0046054 | A1 | 4/2002 | Morand et al. |
| 2003/0040002 | A1 | 2/2003 | Ledley |
| 2003/0055824 | A1 | 3/2003 | Califano |

FOREIGN PATENT DOCUMENTS

| | | |
|---|---|---|
| JP | 11-282740 A | 10/1999 |
| JP | 2001-344340 | 12/2001 |
| JP | 2002-24416 | 1/2002 |
| WO | WO 01/26029 A2 | 4/2001 |
| WO | WO 01/69430 A1 | 9/2001 |
| WO | WO 02/12434 | 2/2002 |
| WO | WO-02/25519 A1 | 3/2002 |
| WO | WO-02/31704 A1 | 4/2002 |
| WO | WO 02/33520 A2 | 4/2002 |
| WO | WO 02/063415 A2 | 8/2002 |

OTHER PUBLICATIONS

"Lecture: The Significance of SNP (single nucleotide polymorphism) at clinical sites"; Gendai Iryo, vol. 32, No. 1, Jan. 10, 2000, pp. 204-210.—(concise explanation of the relevance in English is attached).
"Genome: Gene analysis and computer network"; Iryo to Computer, vol. 12, No. 9, Sep. 20, 2001, pp. 41-49.—(concise explanation of the relevance in English is attached).
Knoppers et al. DNA Sampling and Informed Consent. CMAJ 140 May 1, 1989, 1023-1028.
Moutel et al. Bio-libraries and DNA storage . . . Med Law (2001) 20: 193-204.
Gulcher et al. Protection or privacy by third party encryption in genetic research in Iceland. European Journal o Human Genetics (2000) 8: 739-742.

*Primary Examiner*—Mary K Zeman
(74) *Attorney, Agent, or Firm*—Dickstein Shapiro LLP

(57) ABSTRACT

This invention constructs a highly safe system for processing information for providing semantic information and/or information associated with the semantic information useful for each individual organism through effective utilization of differences in nucleotide sequence-related information among individual organisms. This system comprises steps of: (a) obtaining positional information representing a position in a nucleotide sequence in accordance with a request for an object and/or service; and (b) evaluating adequacy of transmission of nucleotide sequence-related information corresponding to the positional information obtained in step (a), based on the flag information associated with the positional information for evaluating adequacy of transmission of nucleotide sequence-related information associated with the positional information representing a position in a nucleotide sequence.

8 Claims, 16 Drawing Sheets

Fig. 3

| Polymorphism address | ...... | Polymorphism classification | Polymorphism pattern | Classification (name of disease) | Annotative information on the polymorphism pattern (morbidity rate) | ...... | Level of disclosure (disclosability) |
|---|---|---|---|---|---|---|---|
| 123456 | ...... | SNP | A | hypertension | a | ...... | O |
| 123456 | ...... | SNP | G | hypertension | b | ...... | O |
| 223456 | ...... | SNP | G | large-boowel cancer | (i) | ...... | O |
| 223456 | ...... | SNP | A | large-bowel cancer | (ii) | ...... | O |
| 234567 | ...... | SNP | G | stomach cancer | c | ...... | O |
| 234567 | ...... | SNP | A | stomach cancer | d | ...... | O |
| 334567 | ...... | SNP | A | asthma | (iii) | ...... | O |
| 334567 | ...... | SNP | G | asthma | (iv) | ...... | O |
| 345678 | ...... | SNP | C | diabetes | e | ...... | O |
| 345678 | ...... | SNP | T | diabetes | f | ...... | O |
| 445678 | ...... | SNP | T | lung cancer | (I) | ...... | O |
| 445678 | ...... | SNP | C | lung cancer | (II) | ...... | O |
| 456789 | ...... | SNP | T | pollinosis | g | ...... | O |
| 456789 | ...... | SNP | C | pollinosis | h | ...... | O |
| : | : | microsatellite | 14 times | immedicable disease | — | : | × |
| : | : | microsatellite | 9 times | immedicable disease | — | : | × |
| : | : | deletion | G | : | : | : | O |
| : | : | deletion | deletion | : | : | : | O |

| Gno. | Date of birth |
|---|---|
| 0001 | ..**** |

II

| Polymorphism address | Polymorphism pattern | Flag information | Comment |
|---|---|---|---|
| 000001 | G | | ...... |
| 000002 | T | | ...... |
| : | : | : | : |
| 123456 | A | | ...... |
| : | : | : | : |
| 223456 | G | | ...... |
| : | : | : | : |
| 234567 | G | | ...... |
| : | : | : | : |
| 334567 | G | | ...... |
| : | : | : | : |
| 345678 | C | | ...... |
| : | : | : | : |
| 445678 | T | | ...... |
| : | : | : | : |
| 456789 | T | | ...... |
| 456790 | G | | ...... |
| 456791 | 14 times | N | ...... |
| 456792 | deletion | | ...... |
| : | : | : | : |
| 666666 | A | N | ...... |
| : | : | : | : |
| 777777 | G | N | ...... |
| : | : | : | : |
| 888888 | C | N | ...... |
| : | : | : | : |

III

| Anamnesis |
|---|
| infantile asthma |
| gout |
| pollinosis |
| gastric ulcer |
| atopy |
| hypertension |
| diabetes |

IV

| Characteristics | Record |
|---|---|
| blood type | ...... |
| body height | ...... |
| body weight | ...... |
| vision | ...... |
| running ability | ...... |
| psychological test | ...... |
| : | : |

V ......

| (clinical record, etc.) |
|---|
| ...... |
| ...... |
| ...... |
| ...... |
| ...... |
| ...... |
| ...... |

Fig. 7

| Gno. | 0001 | |
|---|---|---|
| Item | Mandatorily set item | Arbitrarily set item (Result of IC) |
| IQ | N | |
| Lifespan | N | |
| Immedicable disease | | N |
| Large-bowel cancer | | |
| Breast cancer | | |
| : | | |

Fig. 8

| Polymorphism address | Item |
|---|---|
| 000001 | |
| 000002 | |
| ⋮ | |
| 111111 | IQ |
| ⋮ | |
| 222222 | Lifespan |
| ⋮ | |
| 333333 | IQ |
| ⋮ | |
| 444444 | Lifespan |
| ⋮ | |
| 456791 | Immedicable disease |
| ⋮ | |
| 555555 | Immedicable disease |
| ⋮ | |
| 600000 | |
| ⋮ | |
| 666666&777777&888888 | Immedicable disease |
| ⋮ | |
| 900000 | |
| 900001 | |
| ⋮ | |

Fig. 13

| Polymorphism address | Flag information |
|---|---|
| 000001 | |
| 000002 | |
| ⋮ | |
| 111111 | N |
| ⋮ | |
| 222222 | N |
| ⋮ | |
| 333333 | N |
| ⋮ | |
| 444444 | N |
| ⋮ | |
| 456791 | N |
| ⋮ | |
| 555555 | N |
| ⋮ | |
| 600000 | |
| ⋮ | |
| 666666&777777&888888 | N |
| ⋮ | |
| 900000 | |
| 900001 | |
| ⋮ | |

INFORMATION PROCESSING SYSTEM USING NUCLEOTIDE SEQUENCE-RELATED INFORMATION

This application is a continuation application of U.S. application Ser. No. 10/534,979, filed May 16, 2005, now U.S. Pat. No. 7,337,071 which is hereby incorporated herein by reference in its entirety.

FIELD OF THE INVENTION

The present invention relates to an information processing system that provides information through a communication network.

BACKGROUND TECHNIQUE

Currently, genomic nucleotide sequences of various organisms including humans are being rapidly determined and information on genomic nucleotide sequences is being accumulated in various databases. For example, currently in progress is the construction of a system which will enable various research institutes and researchers to utilize information on genomic nucleotide sequences accumulated in databases through an information network such as the Internet.

At the same time, research for the purpose of genomic drug discovery and analysis of genetic information and the like have been actively conducted using nucleotide sequences contained in such information on genomic nucleotide sequences, and differences in nucleotide sequences among individual organisms represented by the single nucleotide polymorphism are attracting attention. In general, differences in nucleotide sequences among individual organisms refer to a polymorphism defined by existence of a predetermined nucleotide difference at a frequency of 1% or more in an individual species and a variation defined by a predetermined nucleotide difference of less than 1% in an individual species. In particular, known polymorphisms are SNP (single nucleotide polymorphism), in which there is one nucleotide difference among individual organisms; an insertion/deletion polymorphism, in which one to several tens of nucleotides (sometimes several thousands of nucleotides) have been deleted or inserted; VNTR (variable number of tandem repeat), in which the number of repetitions of a sequence comprising two to several tens of nucleotides as one unit varies; and a microsatellite polymorphism (a repetition sequence having about two to four nucleotides).

Such polymorphisms sometimes affect, for example, differences in amino acid sequences of proteins among individual organisms or differences in expression efficiency concerning predetermined genes among individual organisms. Such influences cause, for example, differences in the morbidity rate of predetermined diseases among individual organisms or differences in sensitiveness to predetermined medicaments among individual organisms.

A system, however, which provides semantic information useful for each organism among a plurality of individual organisms through effective utilization of differences in nucleotide sequence-related information, such as a polymorphism, is not yet constructed.

DISCLOSURE OF THE INVENTION

Under the above circumstances, the present invention is directed to construction of a highly safe system for processing information for providing semantic information and/or information associated with the semantic information useful for each individual organism through effective utilization of differences in nucleotide sequence-related information among individual organisms.

In the method for processing information on nucleotide sequence according to the present invention, whereby the above objects have been accomplished, adequacy of transmission of nucleotide sequence-related information corresponding to positional information is evaluated based on the flag information associated with the positional information. Specifically, the flag information is associated with the positional information and explains adequacy of transmission of nucleotide sequence-related information corresponding to the positional information.

In the method for processing information on nucleotide sequence according to the present invention, processing of positional information corresponding to nucleotide sequence-related information is preferably cancelled when transmission thereof has been evaluated to be inadequate based on the flag information with the use of the positional information and nucleotide sequence-related information corresponding thereto.

In the method for processing information on nucleotide sequence according to the present invention, the flag information and/or information associated with the flag information may be obtained, and adequacy of transmission of nucleotide sequence-related information may be evaluated based on the obtained flag information and/or information associated with the flag information.

In the method for processing information on nucleotide sequence according to the present invention, the flag information may be gradationally set in accordance with the destination of nucleotide sequence information. The flag information may be associated with each piece of positional information or a combination of a plurality of pieces of positional information. The flag information is preferably rewritable and adequately updated.

The method for processing information on nucleotide sequence according to the present invention can be executed in the form of a program that allows a computer comprising hardware, such as a control unit, a transmitter/receiver, and a memory unit, to execute each step of information processing. The method for processing information on nucleotide sequence according to the present invention can be also executed in the form of a recording medium comprising a program that allows a computer comprising hardware, such as a control unit, a transmitter/receiver, and a memory unit, to execute each step of information processing. Further, the method for processing information on nucleotide sequence according to the present invention can be executed in the form of an information processor comprising hardware, such as a control unit, a transmitter/receiver, and a memory unit, that executes each step of information processing.

In addition, the present invention also includes constitutions as disclosed in each claim.

This description includes part or all of the contents as disclosed in the description and/or drawings of Japanese Patent Application No. 2002-334161, which is a priority document of the present application.

BRIEF DESCRIPTION OF THE DRAWINGS

FIG. 3 shows an embodiment of data that is recorded in a main database ("database" is hereinafter abbreviated to "DB").

FIG. 5 shows an embodiment of data recorded on a genome-related information recording medium.

FIG. 7 shows an embodiment of data recorded in an IC table.

FIG. 8 shows an embodiment of data recorded in a table showing polymorphism address-item correlation.

FIG. 13 shows an embodiment of data recorded in a database, in which a polymorphism address is associated with flag information, of a computer used for providing flag information.

DESCRIPTION OF REFERENCE NUMERALS

1: Communication network
2: Shared computer
3: Personal computer
W: Computer used for providing flag information

PREFERRED EMBODIMENTS OF THE INVENTION

Hereafter, the present invention is described in detail with reference to the drawings.

1. First Embodiment

A system for processing information that provides a morbidity rate of a predetermined disease to a user is described as the first embodiment to which the present invention has been applied. Specifically, it is described with reference to the case where a user "requests an object and/or service," such as his/her morbidity rate relating to a predetermined disease. The present embodiment is directed to explaining a system for processing information that utilizes flag information for evaluating adequacy of transmission of nucleotide sequence-related information in which a user possesses such flag information. For the convenience of explanation, this system is explained as a simple model. "An object and/or service" is not limited to the aforementioned, and it includes, for example, objects such as pharmaceutical products, foods, and nonessential grocery items that suit individuals' (individual organisms') diatheses and services such as information that suits individuals' (individual organisms') diatheses and properties.

Figure 1:
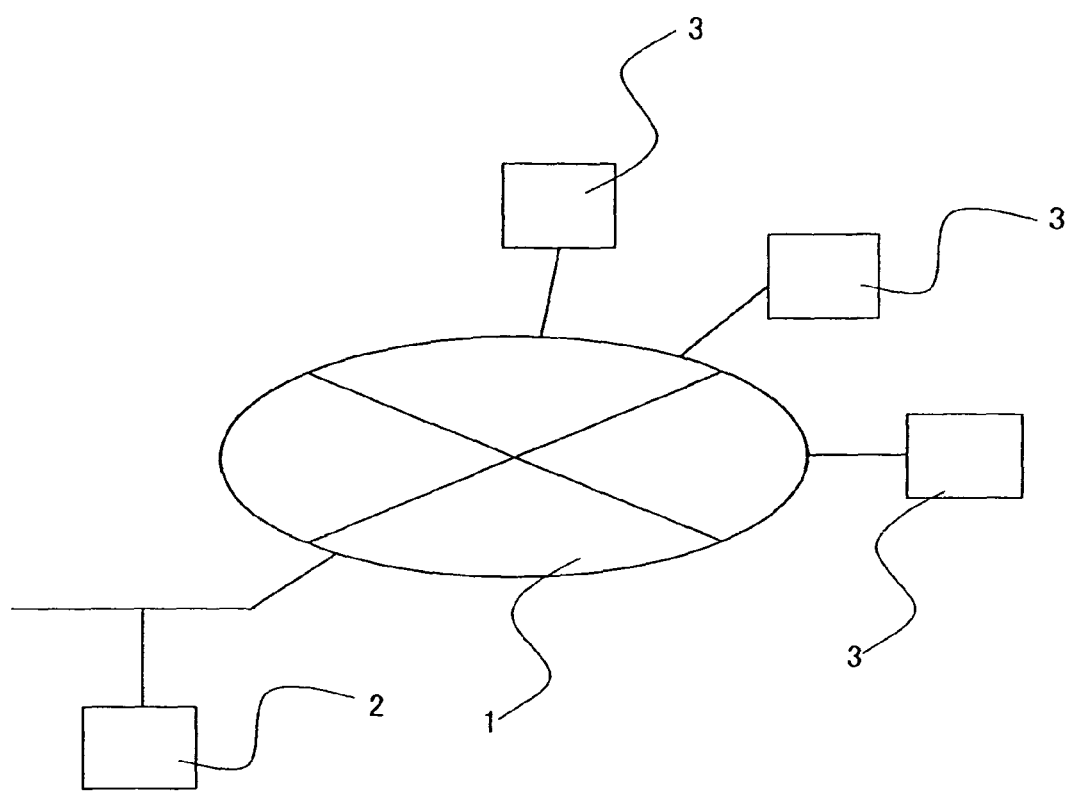
FIG. 1 schematically shows a construction of a system for providing information to which the present invention has been applied.

As shown in FIG. 1, the system for processing information comprises a communication network 1, such as the Internet, a shared computer 2 connected to communication network 1, and at least one personal computers 3 connected to communication network 1, and enables data communication between shared computer 2 and personal computers 3 through communication network 1.

Figure 2:
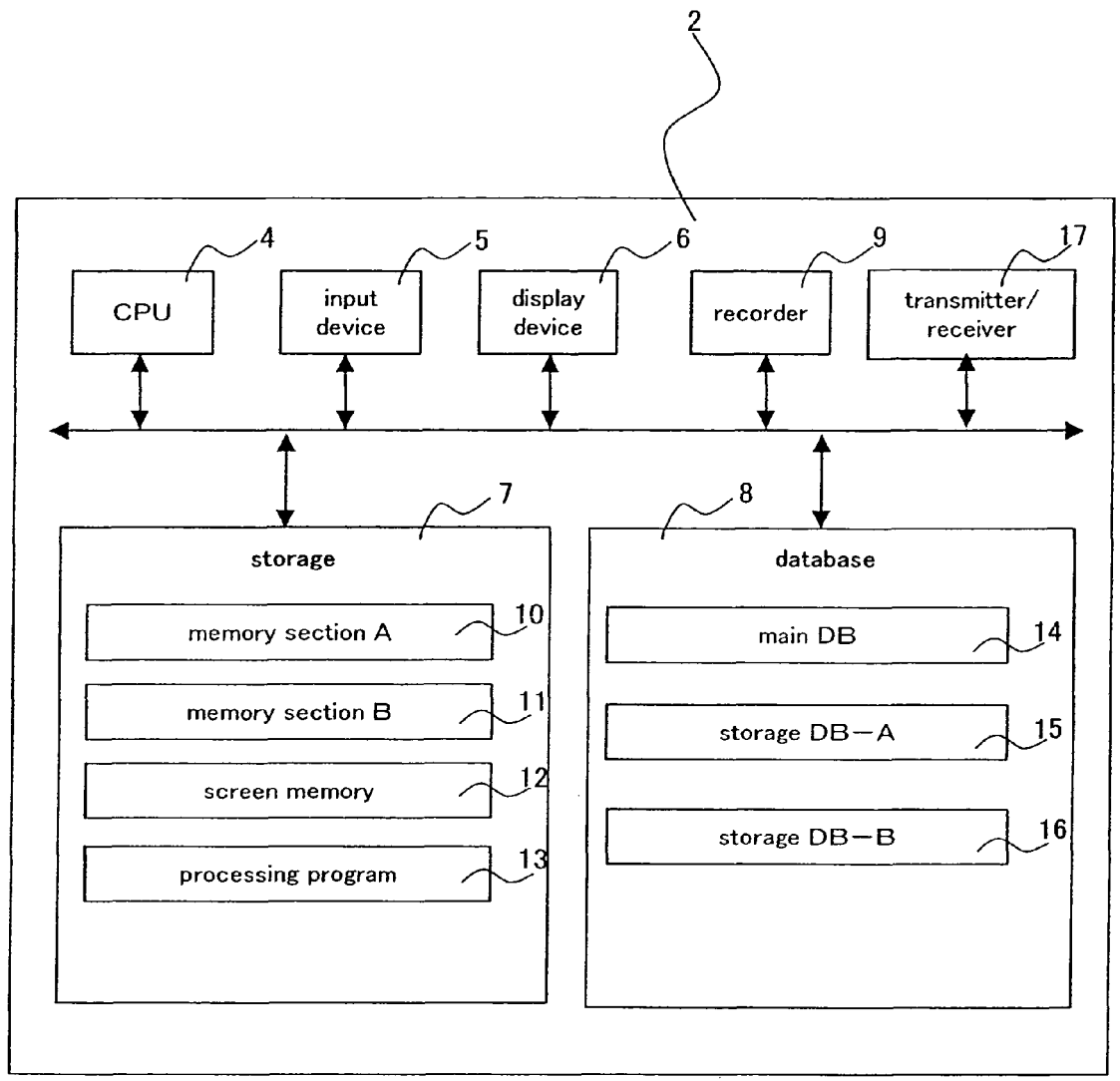
FIG. 2 schematically shows a construction of a shared computer.

As shown in FIG. 2, shared computer 2 is constituted by a CPU 4 that totally controls the operation of the shared computer 2; an input device 5, such as a keyboard and a mouse, with which information, instructions for executing a program and the like can be input; a display device 6 such as a display apparatus; a storage 7 in which temporary information, unrewritable information and the like are recorded; a database 8 for storing various data; a recorder 9 for writing predetermined information in storage 7 and database 8; and a transmitter/receiver 17 for transmission and reception of information to and from personal computers 3 through communication network 1.

Storage 7 in shared computer 2 is constituted by a memory section A10 and a memory section B11 which respectively record different types of information; a screen memory 12 having recorded therein screen data displayed, for example, on personal computer 3 or display device 6; and a processing program 13 for operating the system. Shared computer 2 may have screen memory 12, processing program 13 and the like in an external recording apparatus (not shown) connected to shared computer 2 through communication network 1 instead of containing those in storage 7 inside shared computer 2.

Database 8 in shared computer 2 is constituted by a main DB 14 in which a polymorphism address, a polymorphism pattern, and semantic information are recorded; a storage DB-A15 for saving information recorded in memory section A10; and a storage DB-B16 for saving information recorded in memory section B11. As shown in FIG. 3, polymorphism addresses, a plurality of possible polymorphism patterns in the polymorphism address respectively, and semantic information implied by each of the plurality of polymorphism patterns respectively are stored in association with one another in main DB 14. Main DB 14 may also have recorded therein semantic information implied by a combination of polymorphism patterns in a plurality of polymorphism addresses (such as haplotype).

The "polymorphism address (positional information)" refers to, at least, a position in a nucleotide sequence where a polymorphism is present. In general, the term "polymorphism" includes, for example, a so-called SNP (single nucleotide polymorphism), RFLP (restriction fragment length of polymorphism), VNTR (variable number of tandem repeat), and microsatellite. However, the term "polymorphism" used herein is not limited to these and also includes a variation in nucleotides and nucleotide sequences existing only at a frequency of less than 1% in an individual species. Therefore, "polymorphism address" also includes a position in a nucleotide sequence which indicates a variation of a nucleotide and nucleotide sequences existing only at a frequency of less than 1% in an individual species. Specifically, the "polymorphism address" indicates a position representing a polymorphism or the like by a combination of numerical values, letters, symbols, and the like. The polymorphism address is not particularly limited, for example, may be represented by a combination of a chromosome number, a symbol indicating a gene having a polymorphism therein, and a numerical value indicating a position of a polymorphism in the gene. Alternatively, it may be a combination of a symbol indicating a gene having polymorphism therein and a numerical value indicating a position of polymorphism in the gene.

Further, a "polymorphism address" may be a notation peculiar to a polymorphism imparted to each polymorphism. When the notation peculiar to a polymorphism is used as a polymorphism address, the polymorphism address does not directly indicate the position in the nucleotide sequence, instead, the position can be indirectly found by the notation peculiar to the polymorphism. Therefore, the "polymorphism address" includes the notation peculiar to the polymorphism.

A "polymorphism pattern (nucleotide sequence-related information)" is information on nucleotide sequences which differ among individual organisms, and contains, at least, a pattern of nucleotides or nucleotide sequences in a polymorphism. In addition, the "polymorphism pattern" includes a pattern of nucleotide and nucleotide sequences existing only at a frequency of less than 1% in an individual species and is not limited to a polymorphism. For example, in a polymorphism address known to have A or G, the "polymorphism pattern" is represented either by "A" or "G".

The "polymorphism pattern" may represent a heterozygote or homozygote in a homologous chromosome. For example, the "polymorphism pattern" can be represented by "AA", "GG", or "AG" in the polymorphism address known to have A or G.

Further, the "polymorphism pattern" may indirectly represent a possible pattern in the predetermined polymorphism address instead of direct representation of patterns. For example, in the polymorphism address known to have A or G the "polymorphism pattern" may be represented by "allele 1" when the polymorphism address has "A" or "allele 2" when the polymorphism address has "G". As described above, when the "polymorphism pattern" can be expressed as "AA", "GG", or "AG", the "polymorphism pattern" may be represented by "α" when expressed as "AA", it may be represented by "β" when expressed as "GG", and it may be represented by "γ" when expressed as "AG".

When the polymorphism is the microsatellite type the "polymorphism pattern" may be represented, for example, by numerical values indicating "the number of repetitions" and when the polymorphism is the insertion/deletion type the "polymorphism pattern" may be represented, for example, by symbols indicating "presence/absence". The "polymorphism pattern" in each polymorphism address may be represented by, for example, "polymorphism 1," "polymorphism 2," or "polymorphism 3," in accordance with given rules and arrangements. For example, it can be represented by "polymorphism 1," "polymorphism 2," or "polymorphism 3," in descending order of frequency regarding the "polymorphism pattern" that can appear in each polymorphism address. In this case, "polymorphism 1" in a polymorphism address is not always the same as that in other polymorphism addresses. Specifically, "polymorphism 1" in a given polymorphism address represents "AA" that can appear with the highest frequency, and "polymorphism 1" in other polymorphism addresses represents "GG" that can appear with the highest frequency.

The term "semantic information" used herein refers to information associated with the "polymorphism pattern," for example, information including responsiveness to medicaments, side-effect caused by medicaments, a risk against diseases and disorders, diatheses and properties, interaction among proteins, and various phenotypes caused by differences in polymorphism patterns. "Semantic information" may directly represent a variety of phenotypes resulting from differences in "polymorphism patterns." Alternatively, it may indirectly represent phenotypes with the use of symbols that indicate such phenotypes or the like. "Semantic information" is a type of information which is corrected and increases in the numbers of types accompanied by progress in research on genome and genetics, and constant updating is preferred. In other words, "semantic information" becomes more accurate through increases and decreases in the amount of information accumulated by updating a database using the results of research on genome and genetics.

Information that is further induced from "semantic information" is "information associated with the semantic information" although it is not directly associated with the "polymorphism pattern." When "semantic information" is a risk against diseases, when the relevant risk exceeds a given standard, for example, specific "medical examination items" are derived. These specific "medical examination items" are "information associated with the semantic information."

In the present embodiment, semantic information is recorded in main DB 14 as "annotative information on the polymorphism pattern" associated with at least the predetermined "polymorphism address" and "polymorphism pattern" as shown in FIG. 3. Also, semantic information is associated with, for example, "polymorphism classification," "classification (name of disease)" and the like corresponding to the predetermined "polymorphism address." Consequently, when a predetermined "polymorphism address" is a predetermined "polymorphism pattern," types of diseases and annotative information (semantic information) on the morbidity rates of diseases can be obtained. For example, semantic information can be associated with a combination of respective polymorphism patterns corresponding to a plurality of polymorphism addresses (such as haplotype). In other words, each combination of polymorphism patterns in a plurality of polymorphism addresses can be respectively associated with annotative information (semantic information) representing different morbidity rates for predetermined diseases. In this case, when a plurality of polymorphism addresses are a combination of predetermined polymorphism patterns, annotative information (semantic information) indicating the morbidity rate of a predetermined disease can be obtained.

Semantic information can be further associated with a "level of disclosure" which is set in accordance with a predetermined standard. For example, a standard in setting a "level of disclosure" can be determined by taking into consideration unpredictable disbenefits and the like for individuals that would be caused by disclosure of semantic information, i.e., the morbidity rate of "classification (name of disease)". In particular, in shared computer 2, a "level of disclosure" can be set such that semantic information, the disclosure of which is inappropriate from the view point of, for example, law, regulations, the behavioral norms of an organization having the shared computer 2 or a contract with the user, is not disclosed. In this case, with this system, annotative information representing a morbidity rate associated with a "level of disclosure" at which disclosure is not possible is not disclosed to users. This can prevent the provision of semantic information which could result in unpredictable disbenefit for users or the disclosure of semantic information to parties other than the contract party.

The system may disclose semantic information having a predetermined "level of disclosure" associated therewith to the user through approval by the user of disclosure of semantic information having a predetermined "level of disclosure" associated therewith through, for example, informed consent.

The "level of disclosure" can be set as a plurality of levels of three or more, for example, "1, 2, 3 . . ." or "a, b, c . . .". In this case, the level can be set on the shared computer 2 side according to the type of user, such as the user's age, the user's qualification, and whether or not a contract exists with the user. The user can select the level of disclosure such that only annotative information is provided which represents the morbidity rate associated with the level of disclosure that is above (or below) the predetermined level of disclosure determined in accordance with the informed consent or the like.

In database 8, for example, data such as nucleotide sequence-related information that is the genetic information of the individual requester utilizing the system can be recorded in storage DB-B16. In storage DB-A15, for example, data such as information distinguishing the requester from others utilizing the system can be recorded. In this way, the separate recording of the genetic information of individuals and the information for specifying individuals in storage DB-A15 and storage DB-B16, respectively, makes it difficult to associate a user's genetic information with data that specifies the user.

Shared computer 2 is not limited to one having database 8 therein, and it may have an external database (not shown) connected to shared computer 2 through communication network 1. Shared computer 2 may have a plurality of databases 8 therein or may have an internal database 8 and an external database connected to shared computer 2 through communication network 1.

Figure 4:
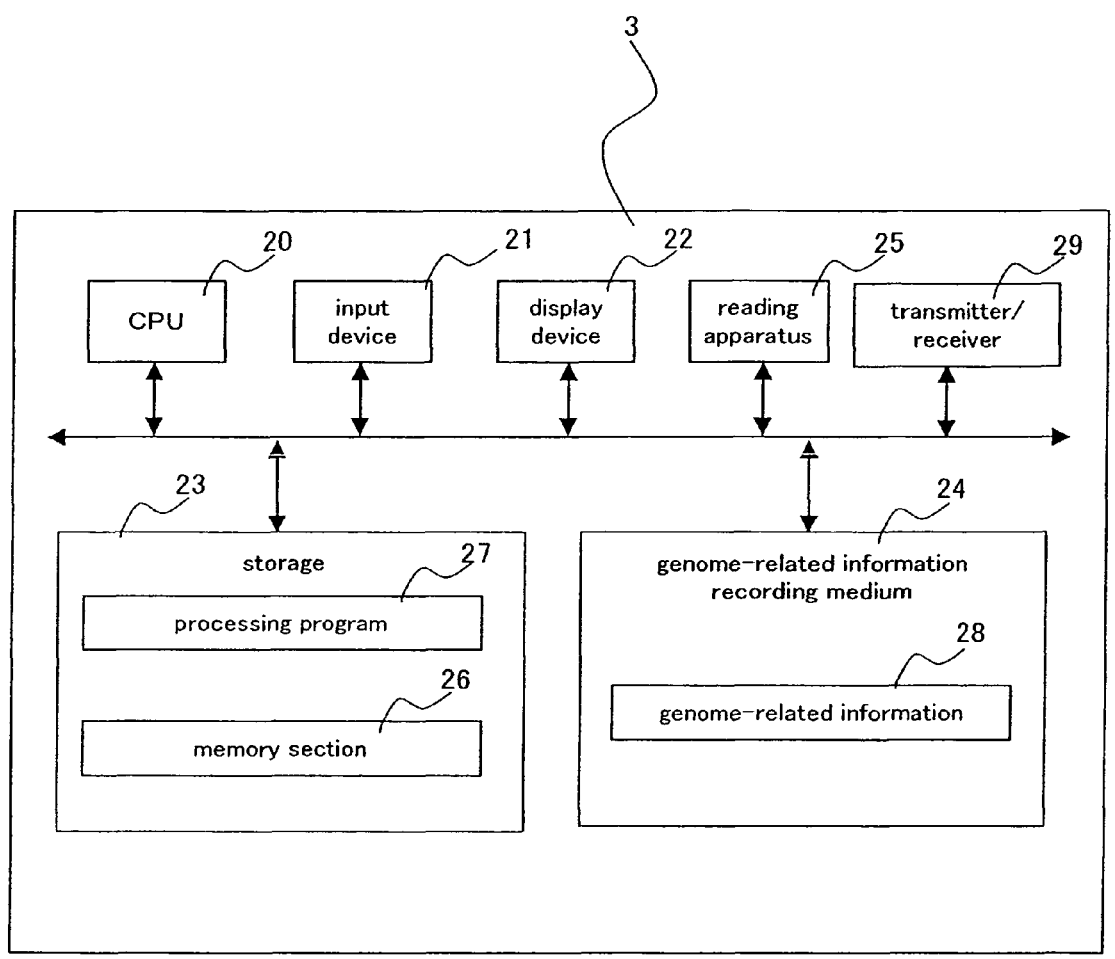
FIG. 4 schematically shows a construction of a personal computer.

As shown in FIG. 4, personal computer 3 is constituted by CPU 20 that totally controls operation of personal computer 3, input device 21 such as a keyboard and a mouse with which information and instructions for executing a program are input, display device 22 such as a display apparatus, storage 23 having temporary information, rewritable information and the like recorded therein, reading apparatus 25 for reading data from genome-related information recording medium 24, and transmitter/receiver 29 for transmitting and receiving information to and from shared computer 2 through communication network 1. Personal computer 3 is not limited to a commonly used computer. For example, it may be any form of cellular phone, personal digital assistance, or other mobile communication tool.

Storage 23 in personal computer 3 has a memory section 26 for recording information provided from genome-related information recording medium 24 and the like, and is recorded a processing program 27 for operating the system for processing information.

Genome-related information recording medium 24 has genome-related information 28 of an individual recorded thereon. Genome-related information recording medium 24 includes, for example, a magnetic recording medium such as a magnetic disk or a magnetic card, an optical recording medium employing such as a magneto-optic recording system or a phase-change recording system, and a semiconductor memory. This genome-related information recording medium 24 may be in any form such as, for example, card, disk, stick, tape, or drum. Further, this genome-related information recording medium 24 may comprise genome-related information 28 of a single individual (an individual organism) recorded thereon. Alternatively, it may comprise a plurality of pieces of genome-related information 28 on a plurality of individuals (individual organisms) recorded thereon.

Genome-related information 28 contained in genome-related information recording medium 24 refers to, at least, a "polymorphism address" and a "polymorphism pattern" in the predetermined polymorphism address obtained as a result of analysis of an individual's (individual organism's) nucleotide sequences, and "flag information" set for each polymorphism address in order to evaluate adequacy of transmission of the polymorphism pattern. Specifically, polymorphism pattern and flag information are associated with polymorphism address. Genome-related information 28 may contain various information, such as information concerning anamnesis, characteristics, an individual's clinical record, or a result of medical examination.

On genome-related information recording medium 24, recorded as genome-related information 28 is, for example, as shown in FIG. 5, the individual's number "Gno." (G number) peculiar to genome-related information 28 as well as the individual's information, such as date of birth, as data I; polymorphism addresses, polymorphism patterns and flag information as data II; anamnesis information as data III; characteristics as data IV; and information concerning the individual's clinical record and the like as data V. In other words, genome-related information 28 is constituted by data I, data II, data III, data IV, and data V. Data I and data II contain essential information and data III, data IV, and data V are respectively constituted by additional information. Additional information concerning a predetermined polymorphism address may be recorded as data II as a "comment" while being linked with a "polymorphism address."

In particular, genome-related information recording medium 24 having "flag information" recorded as data II is used in the present embodiment. The "flag information" refers to information that represents adequacy of transmission of a polymorphism pattern corresponding to a predetermined polymorphism address to shared computer 2 via communication network 1. An example of flag information is setting of "on/off" or "1 or 0" concerning a predetermined polymorphism address. For example, transmission of a polymorphism pattern to shared computer 2 is inadequate concerning a polymorphism address having "on" set as flag information. Transmission of a polymorphism pattern to shared computer 2 is adequate concerning a polymorphism address having "off" set as flag information. In order to indicate that transmission of a predetermined polymorphism address and polymorphism pattern is inadequate, "on" is associated with the polymorphism address, for example, such state is represented by "having flag information provided thereon" or "flag information has been provided" in the present description. The polymorphism address with which "on" has been associated as flag information is represented by "the polymorphism address having flag information provided thereon" or "the polymorphism address on which flag information has been provided" herein.

The flag information is not limited to binary information, in which either one of the binary flags, such as "on/off," is related to a predetermined address. In addition, 3 or more gradable values can be set. A specific example of flag information is the case of 5-gradable values from level 1 to level 5. For example, when flag information is set with 5-gradable values from level 1 to level 5, grades are previously set in a variety of shared computers 2. In such a case, flag information, i.e., from level 1 to level 5, corresponds to grades set in the shared computer 2 as the destination. A rule, for example, that flag information preset more than a predetermined level cannot be transmitted to shared computer 2 of a predetermined grade may be set. Thus, the range of the polymorphism address and that of the polymorphism pattern that can be transmitted to each shared computer 2 can be altered when utilizing the present system.

Flag information is preferably provided, for example, on a polymorphism address, disclosure to the public of which is restricted, or on a polymorphism address, disclosure of which is restricted from an ethical point of view. Specifically, flag information is provided on a polymorphism address that is related to, for example, an immedicable disease, lifespan, assessment of abilities such as IQ, or physical distinctions.

Flag information may be updatable. That is, the flag information that has been once provided on a polymorphism address may be cancelled if transmission of a polymorphism pattern of the polymorphism address to shared computer 2 is evaluated as adequate later. An example of such case is a case where an immedicable disease becomes curable later, and thus, the flag information that has been provided on a polymorphism address related to the immedicable disease is cancelled later. In contrast, a new piece of flag information may be provided on the polymorphism address on which flag information has not been provided when transmission thereof to shared computer 2 is evaluated as being inadequate later. An example of such case is a case where a predetermined polymorphism address is later found to be related to an immedicable disease and thus has flag information provided thereon. When flag information is made updatable, accordingly, updating of genome-related information recording medium 24 at an adequate time results in that the genome-related information recording medium 24 possesses new flag information.

Flag information can be set at an organization that produces genome-related information recording medium 24, at an organization that analyzes polymorphism patterns, or at other organizations. Flag information may be set by the organization that produces the genome-related information recording medium 24 simultaneously with the production thereof. Flag information may be set by the organization that analyzes polymorphism patterns simultaneously with the analysis thereof. Alternatively, flag information may be set after the production of genome-related information recording medium 24 by another organization.

Flag information may be provided after informed consent, confirming whether or not flag information should be provided on a predetermined polymorphism address, to the party having genome-related information recording medium 24.

Further, flag information may be provided on a combination of a plurality of polymorphism addresses. Specifically, flag information can be provided, for example, on a combination of polymorphism address a, polymorphism address b, and polymorphism address c (wherein a, b, and c each independently represent a position in a nucleotide sequence). In such a case, combined transmission of polymorphism address a, polymorphism address b, and polymorphism address c to shared computer 2 is inadequate. Also, a combination of one or two polymorphism patterns in polymorphism address a, polymorphism address b, and polymorphism address c can be adequately transmitted to shared computer 2.

Figure 6:
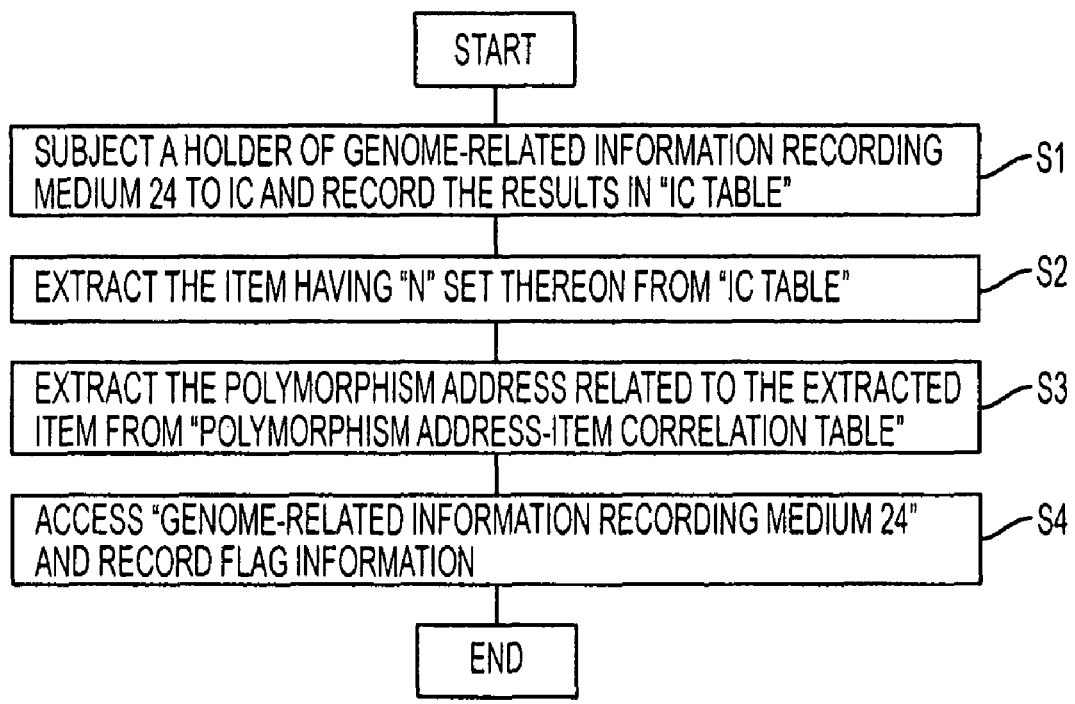
FIG. 6 is a flow chart showing a process for setting flag information on a genome-related information recording medium.

Flag information can be set in accordance with, for example, a process shown in the flow chart shown in FIG. 6. At the outset, in step 1 (S1), a holder of genome-related information recording medium 24 is subjected to informed consent (hereafter abbreviated to "IC") and the result thereof is recorded in the IC table shown in FIG. 7. IC indicates confirmation of an intention to disclose, for example, a polymorphism address, a polymorphism pattern thereof, or the like, which enable evaluation of a morbidity rate of a disease that is hard to cure with modern medical care, to shared computer 2.

As shown in FIG. 7, the correlation between items, such as "IQ," "lifespan," or "immedicable disease," and intention to refuse the disclosure of the polymorphism address and the polymorphism pattern related to the items, which the holder of genome-related information recording medium 24 of a predetermined "Gno." makes, is shown in the IC table. When the holder has intention to refuse the disclosure of the polymorphism address and the polymorphism pattern related to a predetermined item, "N" is recorded as an arbitrarily set item. Regardless of the result of IC, flag information is forcibly set concerning the item, the disclosure of which to shared computer 2 is not allowed, based on laws and other rules.

In step 1, "N" is forcibly set concerning a predetermined item, and "N" is also set concerning an item, disclosure of which is refused by the holder, based on the results of IC. Thus, an IC table that is specific to the holder is prepared.

In step 2 (S2), items concerning which "N" has been set are extracted in accordance with the prepared IC table. In step 3 (S3), polymorphism addresses related to the items extracted in step 2 are extracted from the polymorphism address-item correlation table shown in FIG. 8. The polymorphism address-item correlation table shows the correlation between items in the IC table and polymorphism addresses, based on the results of functional analysis of genetic polymorphisms. Specifically, the polymorphism address-item correlation table comprises polymorphism addresses in association with items related thereto (such as "IQ," "lifespan," or "immedicable disease") recorded therein. When a plurality of polymorphism addresses are related to the item extracted in step 2 in the polymorphism address-item correlation table (when "666666," "777777," and "888888" are related to the item "immedicable disease" in FIG. 8), all the polymorphism addresses related to this item are extracted in step 3.

In step 4 (S4), genome-related information recording medium 24 is accessed to record flag information concerning the polymorphism address extracted in step 3. In step 4, for example, "on" is recorded concerning a polymorphism address that matches the polymorphism address extracted in step 3 from genome-related information recording medium 24, and flag information is provided on the polymorphism address extracted in step 3. When a plurality of polymorphism addresses related to a single item has been extracted in step 3, for example, all the extracted polymorphism addresses have flag information provided thereon.

Thus, genome-related information recording medium 24 comprising flag information can be prepared. The process shown in the above described flow chart can be employed when recording flag information, following the preparation of genome-related information recording medium 24. Alternatively, flag information may be recorded simultaneously with the preparation of genome-related information recording medium 24.

According to the present invention, personal computer 3 and genome-related information recording medium 24 are not limited to the construction as shown in FIGS. 4 and 5 respectively. For example, a genome-related information recording medium may be equipped with a memory section having a processing program and a personal computer may have the genome-related information recording medium mounted thereon to operate the processing program. In this case, a personal computer can be operated in accordance with a processing program recorded in a memory section on a genome-related information recording medium.

Figure 9:
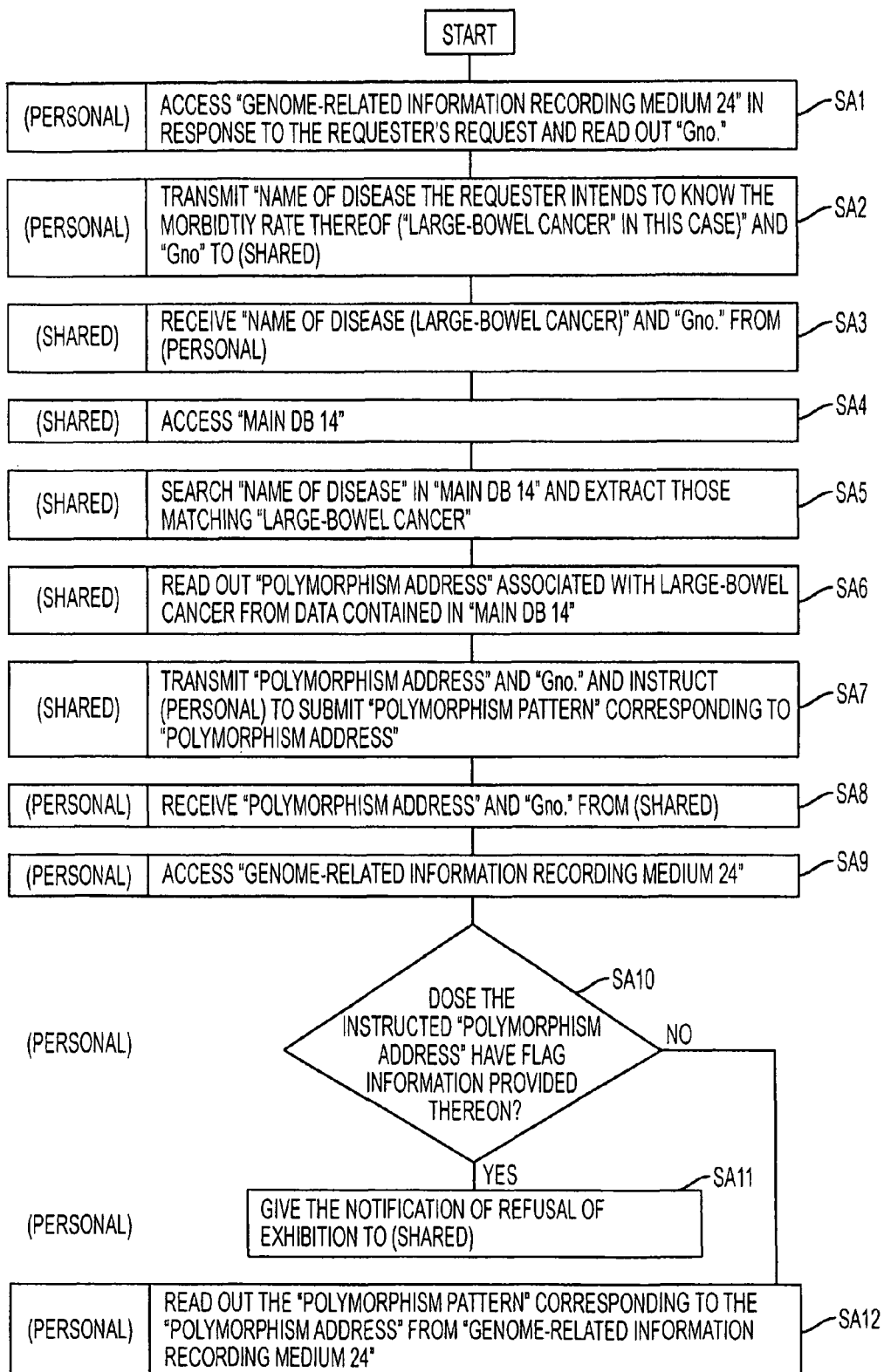
FIG. 9 is a flow chart showing the process in a shared computer and that in a personal computer in a system for providing a morbidity rate of a predetermined disease.
Figure 10:
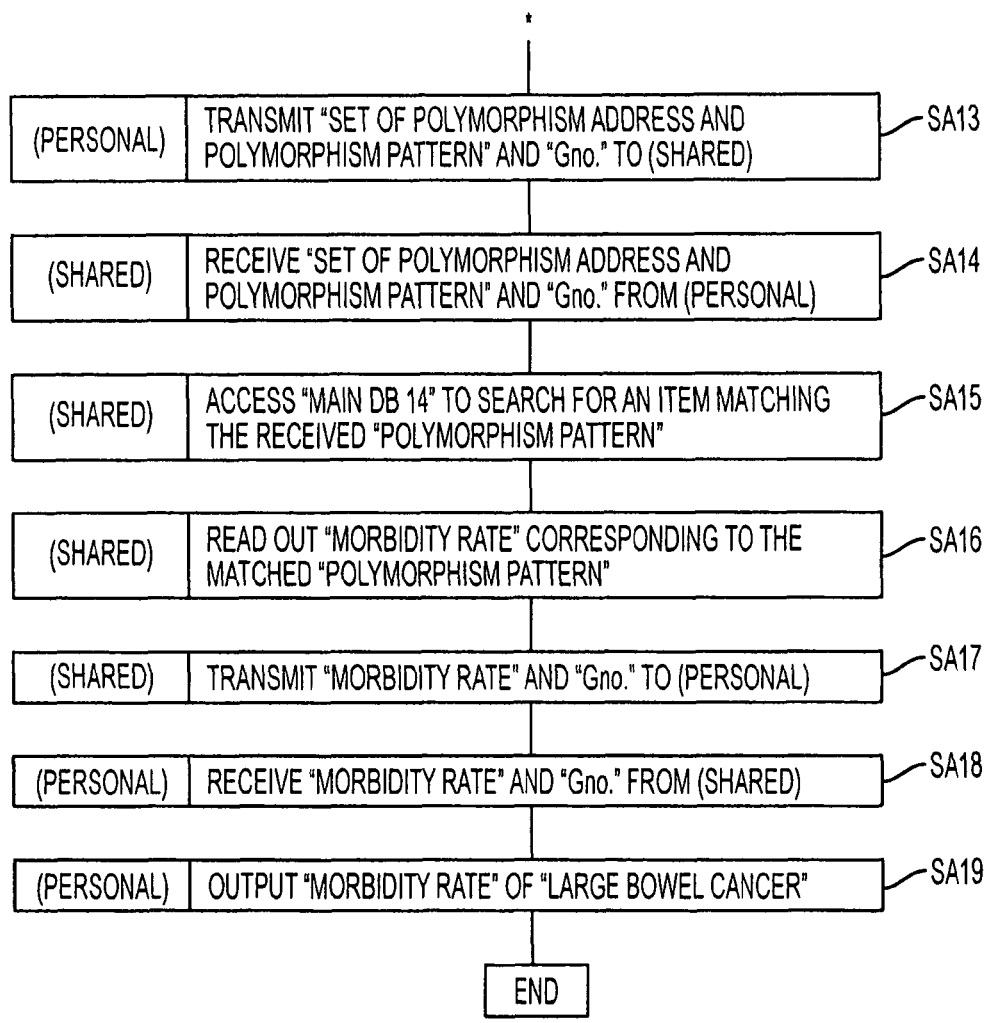
FIG. 10 is a flow chart, which is a continuation of FIG. 9, showing the process in a shared computer and that in a personal computer in a system for providing a morbidity rate of a predetermined disease.

In a system for processing information having the above construction, processing program 13 recorded in storage 7 in shared computer 2 and processing program 27 recorded in storage 23 in personal computer 3 process information in accordance with, for example, flow charts as shown in FIGS. 9 and 10. In the flow charts as shown in FIGS. 9 and 10, a step described as "(shared)" refers to processing in shared computer 2 and a step described as "(personal)" refers to processing in personal computer 3.

The system for processing information is a system in which an individual possessing genome-related information recording medium 24 accesses shared computer 2 using personal computer 3 through communication network 1 and utilizes semantic information recorded in main DB 14 in shared computer 2. The system for processing information may be a system comprising the genome-related information recording medium 24, having genome-related information 28 on a plurality of individuals recorded thereon, to which individuals respectively access.

An individual utilizing this system possesses, for example, genome-related information recording medium 24 comprising flag information. An individual utilizing this system (hereafter referred to as a "requester") first starts processing program 27, which is recorded in storage 23, in step A1 (SA1). Processing program 27 drives reading apparatus 25 in personal computer 3 to access genome-related information recording medium 24. Thus, "Gno." recorded as data I on genome-related information recording medium 24 is read out and the read-out "Gno." is stored in memory section 26.

In step A2 (SA2), based on a screen image displayed by processing program 27 on display device 22, information, the provision of which is desired by the requester wishes to receive, for example, the "morbidity rate of large-bowel cancer" (requested information), is input to personal computer 3. At the same time, the "morbidity rate of large-bowel cancer" and "Gno." are transmitted to shared computer 2 from personal computer 3 through communication network 1. Alternatively, the requester writes the "morbidity rate of large-bowel cancer" and "Gno." in shared computer 2 from personal computer 3 through communication network 1.

In step A3 (SA3), shared computer 2 receives the "morbidity rate of large-bowel cancer" and "Gno." The received "morbidity rate of large-bowel cancer" and "Gno." are stored in memory section A10 as request information.

In step A4 (SA4), upon the reception of request information, processing program 13 recorded in storage 7 is started to access main DB 14. This processing program 13 performs processing in shared computer 2.

In step A5 (SA5), in accordance with processing program 13, "classification (name of disease)" recorded in main DB 14 is searched and information matching with the requested "morbidity rate of large-bowel cancer" (large-bowel cancer) is extracted.

In step A6 (SA6), from among data recorded in main DB 14, a "polymorphism address" associated with "classification (name of disease)" (large-bowel cancer) that matches with the "morbidity rate of large-bowel cancer" is read out. The read-out "polymorphism address" is stored as positional information associated with request information in memory section A10. Specifically, the "morbidity rate of large-bowel cancer" and "polymorphism address" are recorded in memory section A10 in association with a predetermined "Gno."

In step A7 (SA7), "Gno." and "polymorphism address" recorded in memory section A10 are transmitted to personal computer 3 and instruction information instructing submission of a "polymorphism pattern" corresponding to the transmitted "polymorphism address" is transmitted to personal computer 3. At this time, the submission of additional information such as that concerning anamnesis and characteristics may be optionally instructed depending on the types of request information.

In step A8 (SA8), "Gno.," "polymorphism address," and instruction information transmitted from shared computer 2, are received. The received "Gno." and "polymorphism address" are recorded in memory section 26.

In step A9 (SA9), personal computer 3 accesses genome-related information recording medium 24 in order to confirm whether or not the "polymorphism address" contained in the received instruction information has "flag information" provided thereon.

In step A10 (SA10), the polymorphism addresses recorded on genome-related information recording medium 24 are searched to find the polymorphism address that matches the received "polymorphism address," and whether or not the received "polymorphism address" has flag information provided thereon is evaluated. When a plurality of polymorphism addresses are received in step A8, all the polymorphism addresses are inspected in order to evaluate whether or not they have flag information provided thereon. In step A10, when the received polymorphism address has flag information provided thereon, a "yes" evaluation is made. When the received polymorphism address does not have any flag information provided thereon, a "no" evaluation is made. When flag information is provided on a combination of a plurality of polymorphism addresses, such as when flag information is provided on all the polymorphism addresses constituting such combination, a "yes" evaluation is made. When at least one of the polymorphism addresses constituting such combination does not have any flag information, a "no" evaluation is made.

When a "yes" evaluation is made in step A10, the procedure is advanced to step A11 (SA11). When a "no" evaluation is made in step A10, the procedure is advanced to step A12 (SA21).

When a plurality of polymorphism addresses are received in step A8, either of the following evaluation may be made in step A10. A "no" evaluation may be made when none of the polymorphism addresses have flag information provided thereon (evaluation 1). Alternatively, a "yes" evaluation is selectively made concerning the polymorphism address having flag information provided thereon, and a "no" evaluation is made concerning the polymorphism address having no flag information provided thereon, among a plurality of polymorphism addresses (evaluation 2).

When a plurality of polymorphism addresses are received in step A8, evaluation 1 is made in step A10, and at least one of the plurality of received polymorphism addresses has flag information provided thereon, a "yes" evaluation is made and the procedure is advanced to step A11. In such a case, the procedure is advanced to step A12 only when none of the received polymorphism address have flag information provided thereon.

In contrast, when a plurality of polymorphism addresses are received in step A8 and evaluation 2 is made in step A10, a "yes" evaluation is made concerning a polymorphism address having flag information provided thereon among the plurality of received polymorphism addresses. A "no" evaluation is made concerning a polymorphism address having no flag information provided thereon among the plurality of received polymorphism addresses. A procedure concerning the polymorphism address that has received a "yes" evaluation is selectively advanced to step A11, and a procedure concerning the polymorphism address that has received a "no" evaluation is advanced to step A12.

In step A11, notification of refusal of exhibition of polymorphism addresses contained in the instruction information is given to shared computer 2. When evaluation 1 is made in step A10, exhibition of polymorphism patterns corresponding to any polymorphism address is refused and notification of cancellation of the use of the present system is given to shared computer 2 in step A11. When evaluation 2 is made in step A1, exhibition of the polymorphism pattern corresponding to the polymorphism address having flag information provided thereon is refused in step A11, and notification of continuation of the use of the present system is given.

In step A12, genome-related information recording medium 24 is accessed in accordance with processing program 27, data II is searched, a polymorphism pattern in the polymorphism address having no flag information provided thereon is read out, and the polymorphism address is then recorded in memory section 26 in association with the polymorphism pattern. When evaluation 2 is made in step A10, polymorphism patterns are read out and recorded concerning only the polymorphism addresses having no flag information provided thereon among the plurality of received polymorphism addresses in step A12.

In step A12, whether the "Gno." contained in the instruction information is correct or not is preferably confirmed by accessing data I. In step A12, additional information recorded as data III, data IV, and data V is read out simultaneously with the polymorphism pattern and may be optionally recorded in memory section 26.

In step A13 (SA13), the temporarily-recorded polymorphism pattern associated with the polymorphism address and the optionally-recorded additional information in memory section 26 are output to shared computer 2 together with "Gno." through communication network 1. In step A14 (SA14), shared computer 2 receives the polymorphism pattern associated with the polymorphism address and the optionally-recorded additional information, and the received polymorphism pattern is recorded in memory section A10 in association with the polymorphism address.

In this embodiment, shared computer 2 transmits instruction information for exhibition of the "polymorphism pattern" in step A7, and personal computer 3 evaluates whether or not the polymorphism address contained in the instruction information has flag information provided thereon in step A10. The system, however, may not transmit the instruction information in step A7. In this a case, in step A10, personal computer 3 searches for data II based on the polymorphism address received in step A8, and evaluates whether or not the received polymorphism address has flag information provided thereon in accordance with processing program 27.

In step A15 (SA15), main DB 14 is accessed to search information matching with the received polymorphism address and polymorphism patterns. More specifically, a plurality of polymorphism patterns are recorded in main DB 14 for one polymorphism address. Thus, which polymorphism pattern in main DB 14 matches with the received polymorphism address and the polymorphism pattern thereof is searched.

In step A16 (SA16), the morbidity rate of large-bowel cancer (semantic information) which is associated with the polymorphism pattern matching the received polymorphism pattern is read out in accordance with processing program 13. Specifically, in step A16, the morbidity rate of large-bowel cancer of a requester can be read out in accordance with the polymorphism address and polymorphism pattern submitted by the requester. The read-out morbidity rate is stored in memory section A10 in association with the requester's "Gno" and "polymorphism address," and "polymorphism pattern." At this time, the morbidity rate of large-bowel cancer may be corrected in accordance with additional information and then stored. Alternatively, other information obtained from additional information may be stored in association with the requester's "Gno."

When some of the polymorphism addresses and polymorphism patterns among the polymorphism addresses contained in the instruction information are received in step A14, a morbidity rate can be read out with the use of some of the received polymorphism addresses and polymorphism patterns in step A16.

Subsequently, in step A17 (SA17), the requester's "Gno." and morbidity rate, which are stored in memory section A10, are transmitted as semantic information to personal computer 3 through communication network 1. Personal computer 3 receives the requester's "Gno." and morbidity rate (semantic information) in step A18 (SA18). The received semantic information is recorded in memory section 26.

In step A19 (SA19), the morbidity rate of large-bowel cancer is displayed on display device 22 based on semantic information recorded in memory section 26 in accordance with processing program 27. Instead of steps A17 to A19, shared computer 2 can read out (prepare) a screen that displays semantic information in accordance with processing program 13, and display it on display device 22 of personal computer 3 through communication network 1. Also in this case, semantic information is considered to be transmitted from shared computer 2 to personal computer 3. As a result, the requester can obtain the morbidity rate of large-bowel cancer using genome-related information 28 recorded on genome-related information recording medium 24.

When "information associated with semantic information" is further drawn out from "semantic information" that has been read out in step A16, "semantic information" and "information associated with the semantic information" are transmitted in association with the polymorphism address in step A17, and they are received in step A18 and "semantic information" and "information associated with the semantic information" are displayed in step A19 in the same manner.

In this system, in case that information concerning the provision of "functional foods that prevent large-bowel cancer" is further received in step A3 as requested information in addition to "the morbidity rate of large-bowel cancer" requested by the requester when, for example, the morbidity rate exceeds a given standard, the requested functional foods can be provided together with information concerning the morbidity rate of large-bowel cancer of the requester when the morbidity rate exceeds a given standard.

Up to steps A3 to A7 and step A14 in shared computer 2 may be carried out with an organization different from that of steps A14 to A17. In such a case, steps that are carried out in shared computer 2 are divided into two parts.

A polymorphism pattern may or may not be encrypted in this system.

As mentioned above, utilization of genome-related information recording medium 24, which has individuals' polymorphism patterns in association with polymorphism addresses and flag information recorded thereon, enables individuals to use semantic information recorded in main DB 14 through the polymorphism addresses in this system. In other words, an individual utilizing this system does not have to record semantic information on a genome-related information recording medium. Instead, the individual can obtain various semantic information simply by possessing genome-related information 28 having the polymorphism pattern associated with the polymorphism address.

In the present system, flag information is associated with the polymorphism address. Thus, whether or not a polymorphism pattern to be transmitted corresponds to a polymorphism address having flag information provided thereon or a polymorphism address having no flag information provided thereon is evaluated. Thus, leakage of polymorphism addresses and polymorphism patterns that should not be transmitted via communication network 1 can be prevented with the present system.

In this system, transmission of polymorphism addresses and polymorphism patterns can be regulated in accordance with a type of shared computer 2 (including a type of business and the presence or absence of public authorization) and the like by setting 3 or more gradable values as flag information. In other words, the setting of 3 or more gradable values as flag information enables evaluation concerning adequacy of transmission of polymorphism addresses and polymorphism patterns for every shared computer 2 as a destination in the present system. Thus, inadequate leakage of polymorphism addresses and polymorphism patterns can be prevented.

Figure 11:
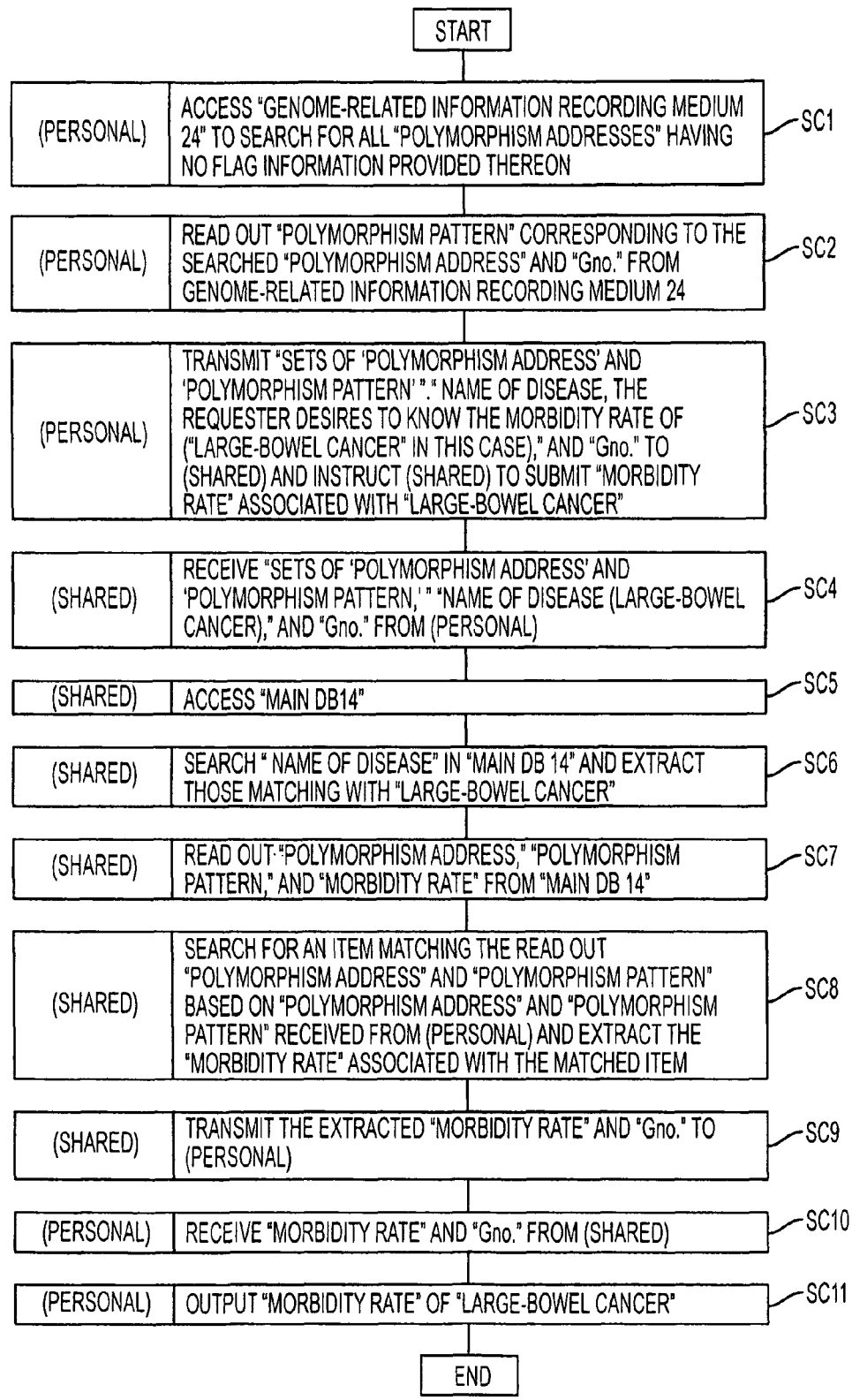
FIG. 11 is a flow chart showing another process in a shared computer and that in a personal computer in a system for providing a morbidity rate of a predetermined disease.

In the system for processing information, processing program 13 recorded in storage 7 of shared computer 2 and processing program 27 recorded in storage 23 of personal computer 3 may process information in accordance with, for example, the flow chart shown in FIG. 11. Also in the flow chart shown in FIG. 11, a step described as "(shared)" refers to processing in shared computer 2 and a step described as "(personal)" refers to processing in personal computer 3.

When utilizing the system, the requester first starts processing program 27 recorded in storage 23 in step C1 (SC1). Processing program 27 drives reading apparatus 25 in personal computer 3 and accesses genome-related information recording medium 24, and searches for a polymorphism address having no flag information provided thereon from among all the "polymorphism addresses" recorded as data II. The polymorphism address having no flag information provided thereon that had been attained as a result of search is stored in memory section 26.

Subsequently, the polymorphism address searched for in step C1, a polymorphism pattern corresponding thereto, and "Gno." are read out with the use of reading apparatus 25 in step C2 (SC2). The read-out "Gno.," "polymorphism address," and "polymorphism pattern" are stored in memory section 26.

In step C3 (SC3), based on a screen image displayed in accordance with processing program 27 on display device 22, information which the requester wishes to receive, for example the "morbidity rate of large-bowel cancer" (request information), is input to personal computer 3. At the same time, the "morbidity rate of large-bowel cancer" and "Gno.", "polymorphism address," and "polymorphism pattern" recorded in memory section 26 are transmitted to shared computer 2 from personal computer 3 through communication network 1.

In step C4 (SC4), shared computer 2 receives "morbidity rate of large-bowel cancer," "Gno.", "polymorphism address," and "polymorphism pattern." The received "morbidity rate of large-bowel cancer" is recorded as request information in memory section A10 and "Gno.", "polymorphism address" and "polymorphism pattern" are also stored in memory section A10. Shared computer 2 starts processing program 13 upon reception of the request information and, in step C5 (SC5), accesses main DB 14 in accordance with processing program 13.

In step C6 (SC6), in accordance with processing program 13, "classification (name of disease)" recorded in main DB 14 is searched and classification matching with the requested "morbidity rate of large-bowel cancer" (large-bowel cancer) is extracted.

In step C7 (SC7), the "polymorphism address" classified as "large-bowel cancer," all the "polymorphism patterns" associated with the polymorphism address, and the "morbidity rate" in all the polymorphism patterns are read out from main DB 14 in accordance with processing program 13. The read-out "polymorphism address," "polymorphism pattern," and "morbidity rate" are stored in memory section A10.

In step C8 (SC8), the data stored in memory section A10 in step C7 is searched based on the "polymorphism address" and the "polymorphism pattern" received in step C4, and a morbidity rate associated with polymorphism pattern matching with the received "polymorphism pattern" is extracted from memory section A10.

In step C9 (SC9), the result of step C8, that is, the morbidity rate extracted according to which polymorphism pattern in main DB 14 matches with the polymorphism pattern contained in the received information in step C4, is transmitted to personal computer 3 through communication network 1. In this case, shared computer 2 transmits the extracted morbidity rate together with the requester's "Gno."

In step C10 (SC10), the "Gno." and "morbidity rate (semantic information)" transmitted from shared computer 2 is received. The received "Gno." and "morbidity rate" are recorded in memory section 26. At this time, data I recorded on genome-related information recording medium 24 is accessed and whether the received "Gno." is correct or not can be confirmed.

In step C11 (SC11), in accordance with processing program 27, the morbidity rate of large-bowel cancer is displayed on display device 22 based on semantic information recorded in memory section 26. Instead of steps C9 to C11, shared computer 2 can read out (prepare) a screen that displays semantic information in accordance with processing program 13, and display it on display device 22 of personal computer 3 through communication network 1. Also in this case, semantic information is considered to be transmitted from shared computer 2 to personal computer 3. This enables the requester to obtain the morbidity rate of large-bowel cancer using genome-related information 28 recorded on genome-related information recording medium 24.

More particularly, in accordance with the process of the flow chart shown in FIG. 11, all the polymorphism addresses having no flag information provided thereon and polymorphism patterns are inputted to shared computer 2 and semantic information to be provided to the requester is obtained in shared computer 2. In accordance with the process of the flow chart shown in FIG. 11, even with a relatively small number of times of reception/transmission of information between personal computer 3 and shared computer 2, the requester can obtain semantic information. Even if the information processing capacity of personal computer 3 is relatively low, therefore, the desired semantic information can be adequately provided in accordance with the process of the flow chart shown in FIG. 11. In addition, the requester can obtain semantic information in a very simple manner.

Further, when the present system is utilized in accordance with the process of the flow chart shown in FIG. 11, leakage of polymorphism addresses and polymorphism patterns that should not be transmitted via communication network 1 can be prevented because of the use of the polymorphism pattern of the polymorphism address on which no flag information has been provided.

When the present system is utilized in accordance with the process of the flow chart shown in FIG. 11, transmission of polymorphism addresses and polymorphism patterns can be regulated in accordance with a type of shared computer 2 (including a type of business and the presence or absence of public authorization) by setting 3 or more gradable values as flag information. In such a case, therefore, setting of 3 or more gradable values as flag information enables evaluation concerning adequacy of transmission of polymorphism addresses and polymorphism patterns for every shared computer 2 as a destination. Thus, inadequate leakage of polymorphism addresses and polymorphism patterns can be prevented.

Meanwhile, in the system for processing information, a recording medium prepared by removing information contained as data II from a genome-related information recording medium; that is, a recording medium having only data I and additionally data III to V, may be used. In this case, information contained as data II is recorded in an external database (genome-related information recording medium) connected to personal computer 3 through communication network 1. In such a system, for example, in step A9 of the flow charts shown in FIGS. 9 and 10, the external database is accessed through communication network 1, a polymorphism pattern in the instructed polymorphism address and the flag information are read out, and the polymorphism address, the polymorphism pattern and the flag information can be recorded in memory section 26 in association with one another. Alternatively, in step C1 of the flow charts shown in FIG. 11, the external database is accessed via communication network 1, the polymorphism patterns and flag information concerning all polymorphism addresses are read out, and the polymorphism address, the polymorphism pattern, and the flag information can be stored in memory section 26 in association with one another. As shown in the processes of the flow charts shown in FIGS. 9 and 10, and the flow chart shown in FIG. 11, respectively, accordingly, the requester can obtain semantic information via this system.

The system for processing information may be equipped with genome-related information recording medium 24 connected to personal computer 3 via communication network 1 instead of the requester has genome-related information recording medium 24 or the recording medium prepared by removing information contained in data II from such genome-related information recording medium. In such a system, the requester can access genome-related information recording medium 24 through communication network 1 to download information such as "polymorphism addresses," "polymorphism patterns," and "flag information" recorded on genome-related information recording medium 24 into personal computer 3. In this case, genome-related information recording medium 24 may comprise genome-related information of a plurality of individuals (each "Gno.") recorded thereon.

In addition, the present invention is not limited to the above-mentioned construction, i.e., shared computer 2 comprising main DB 14. For example, the present invention is applicable to a system for processing information equipped with main DB 14 connected to shared computer 2 via communication network 1. In this case, shared computer 2 accesses main DB 14 through communication network 1 in a manner as shown in the flow charts shown in FIGS. 9 and 10 and the flow chart shown in FIG. 11. In such a case, the requester can also obtain desired semantic information in accordance with the processes of the flow charts shown in FIGS. 9 and 10 or that of the flow chart shown in FIG. 11 according to the system for processing information.

More specifically, shared computer 2 can access a plurality of main DBs 14 owned by different organizations or groups through communication network 1 and can utilize semantic information contained in such plurality of main DBs 14, thereby providing information to the requester. In the system for processing information, shared computer 2 accesses various main DBs 14 containing information concerning the morbidity rate of large-bowel cancer as semantic information in step A4 as shown in the flow charts shown in FIGS. 9 and 10 or in step C5 as shown in the flow chart shown in FIG. 11. According to the system for processing information, therefore, the requester can obtain information concerning the morbidity rate of large-bowel cancer from information contained in a plurality of main DBs 14.

In this system, shared computer 2 may transmit at least the requested information received from personal computer 3 to a so-called agent and obtain semantic information ("morbidity rate of large-bowel cancer" in this embodiment) through the agent as shown in the processes of the flow charts shown in FIGS. 9 and 10 or that of the flow chart shown in FIG. 11.

2. Second Embodiment

Subsequently, a system for providing information such as a morbidity rate of a given disease to a user, wherein a third party other than the user and the information provider possesses flag information, is explained as a second embodiment of the present invention. In the following description, the same appellations, symbols, and definitions are employed for the same constitutions and terms as those of the system for processing information according to the first embodiment, thereby omitting explanation of the constitution, operation, and terms of the system according to the present embodiment. In this embodiment, the system is also explained as a simple model for the convenience of the explanation.

Figure 12:
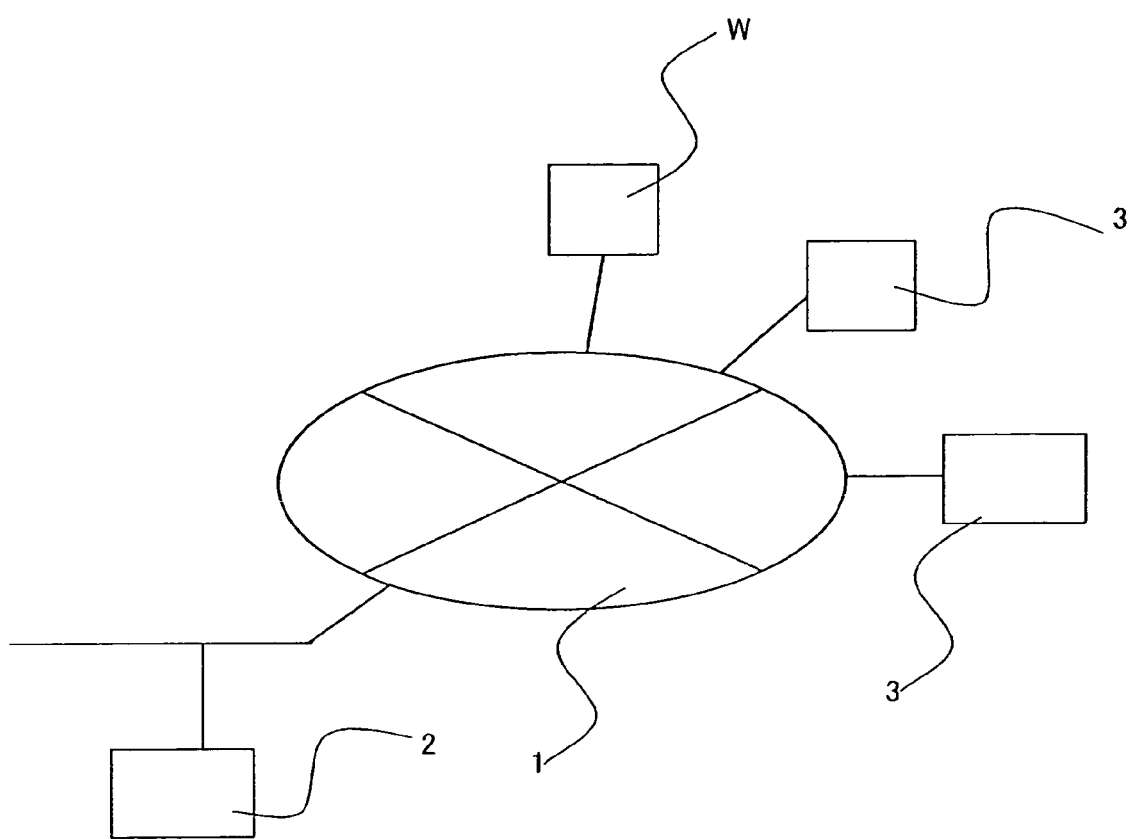
FIG. 12 schematically shows a construction of the system for providing information according to the second embodiment of the present invention.

As shown in FIG. 12, the system for providing information comprises: a communication network 1, such as the Internet; shared computer 2 connected to communication network 1; at least one personal computers 3 connected to communication network 1; and computer W used for providing flag information comprising flag information. This system enables data communication among shared computer 2, personal computers 3, and computer W used for providing flag information via communication network 1.

In the present embodiment, shared computer 2 has a constitution similar to that according to the first embodiment. Personal computer 3 also has a constitution similar to that according to the first embodiment, except that flag information is not recorded on genome-related information recording medium 24.

Computer W used for providing flag information comprises, for example, a database as shown in FIG. 13 in which flag information is associated with polymorphism addresses. The database comprises the flag information explained in the first embodiment in association with the polymorphism addresses recorded therein. In this database, flag information may or may not be related to so-called semantic information, such as a disease, feature, character, lifespan, or IQ, involved with polymorphism addresses.

Flag information is preferably varied in accordance with each genome-related information recording medium 24 in the database. The database may be common among a plurality of or all of genome-related information recording media 24.

Figure 14:
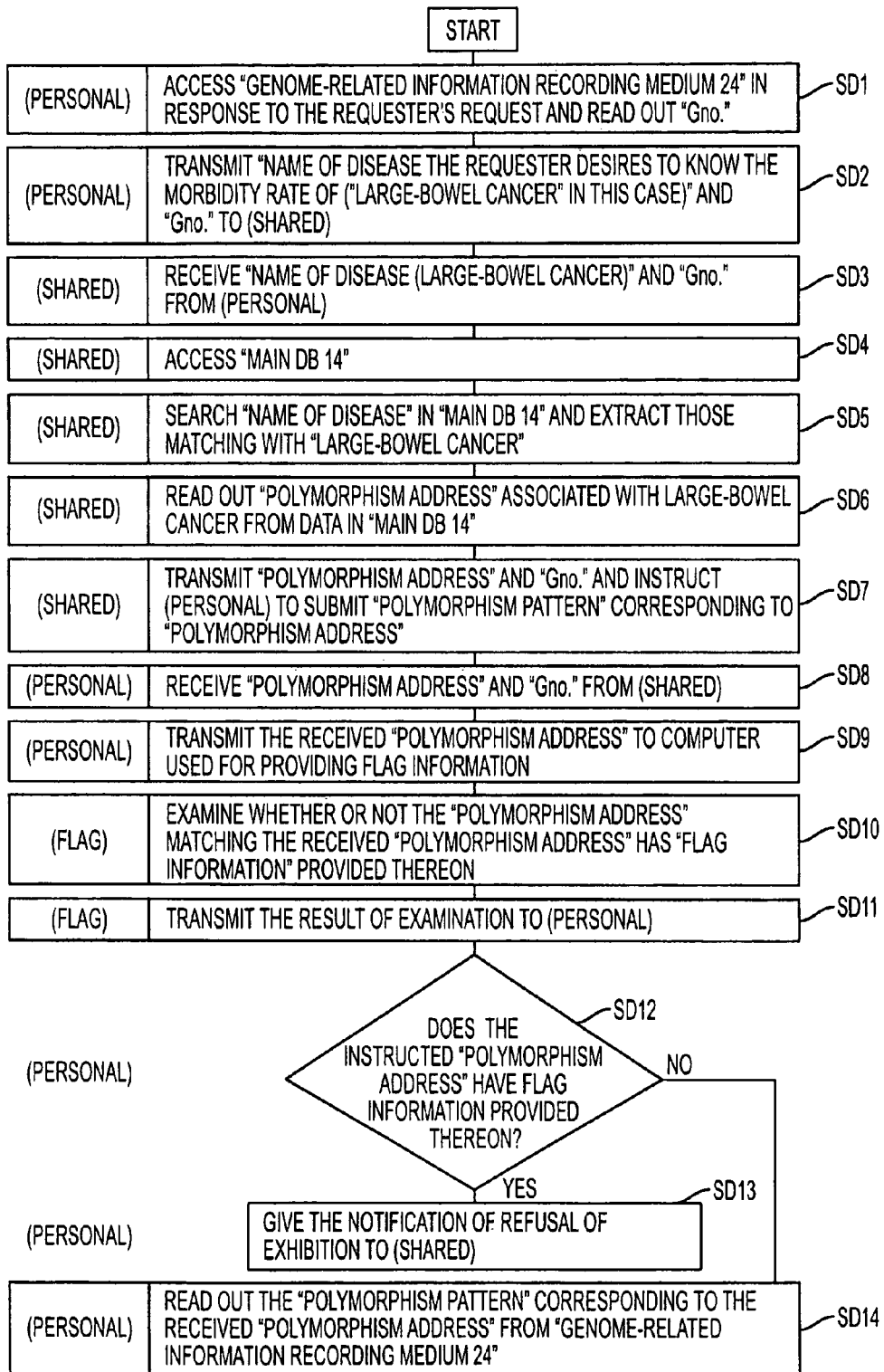
FIG. 14 is a flow chart showing a process in a shared computer, a personal computer and a computer used for providing flag information in the system according to the second embodiment.
Figure 15:
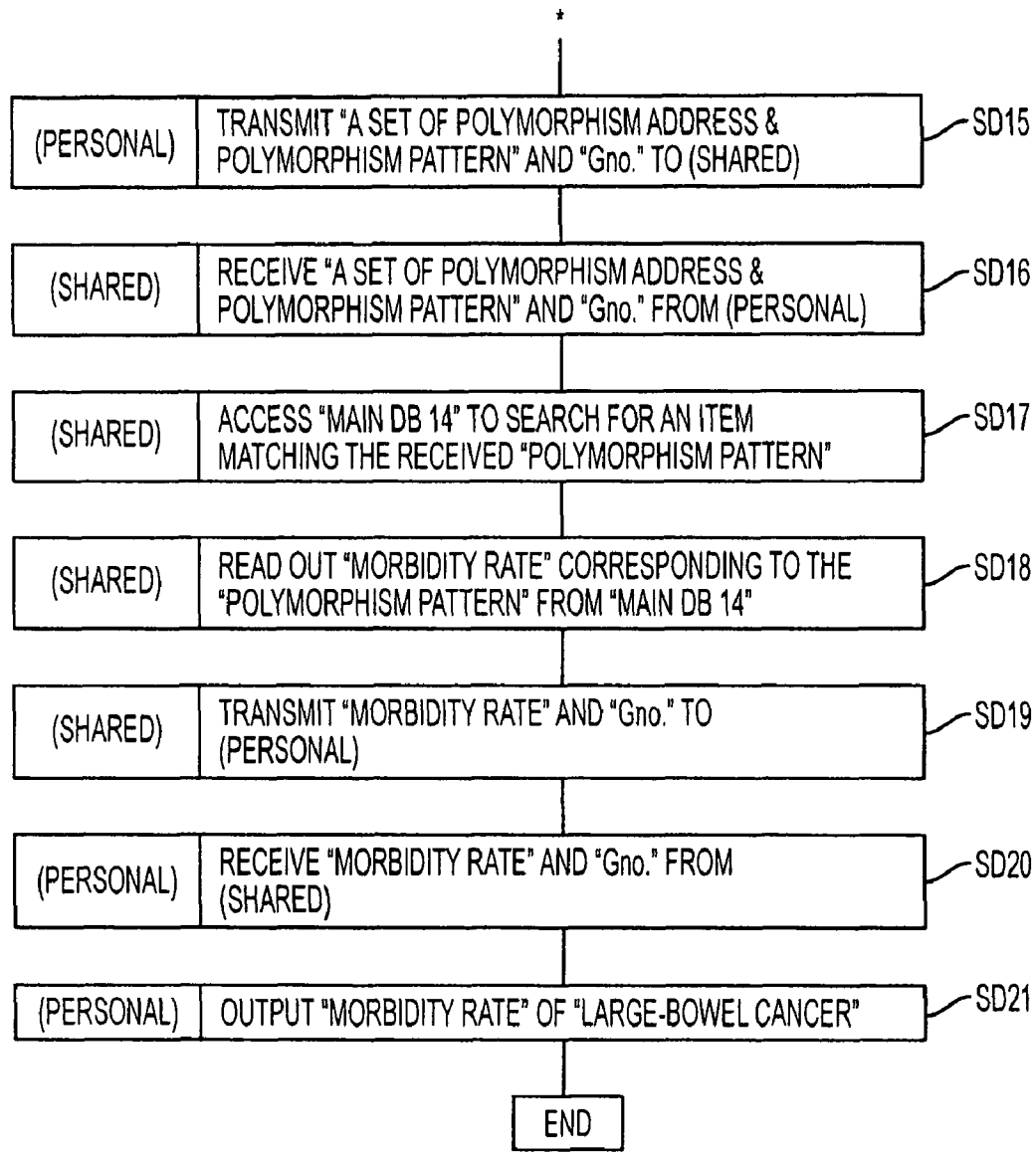
FIG. 15 is a flow chart, which is a continuation of FIG. 14, showing a process in a shared computer, a personal computer and a computer used for providing flag information in the system according to the second embodiment.

This system for providing information processes information in accordance with, for example, the processes of the flow charts shown in FIGS. 14 and 15. In the flow charts as shown in FIGS. 14 and 15, the steps denoted as "(shared)"

refer to processes in shared computer 2, steps denoted as "(personal)" refer to processes in personal computer 3, and the steps denoted as "(flag)" refer to processes in computer W used for providing flag information.

A requester first starts processing program 27, which is recorded in storage 23, in step D1 (SD1). Processing program 27 drives reading apparatus 25 in personal computer 3 to access genome-related information recording medium 24. Thus, "Gno." recorded as data I on genome-related information recording medium 24 is read out and the read-out "Gno." is stored in memory section 26.

In step D2 (SD2), based on a screen image displayed by processing program 27 on display device 22, information, the provision of which is desired by the requester wishes to receive, for example, the "morbidity rate of large-bowel cancer" (requested information), is input to personal computer 3. At the same time, the "morbidity rate of large-bowel cancer" and "Gno." are transmitted to shared computer 2 from personal computer 3 through communication network 1. Alternatively, the requester writes the "morbidity rate of large-bowel cancer" and "Gno." in shared computer 2 from personal computer 3 through communication network 1.

In step D3 (SD3), shared computer 2 receives the "morbidity rate of large-bowel cancer" and "Gno." The received "morbidity rate of large-bowel cancer" and "Gno." are stored in memory section A10 as request information.

In step D4 (SD4), upon the reception of request information, processing program 13 recorded in storage 7 is started to access main DB 14. This processing program 13 performs processing in shared computer 2.

In step D5 (SD5), in accordance with processing program 13, "classification (name of disease)" recorded in main DB 14 is searched and information matching with the requested "morbidity rate of large-bowel cancer" (large-bowel cancer) is extracted.

In step D6 (SD6), from among data recorded in main DB 14, a "polymorphism address" associated with "classification (name of disease)" (large-bowel cancer) that matches with the "morbidity rate of large-bowel cancer" is read out. The read-out "polymorphism address" is stored as positional information associated with request information in memory section A10. Specifically, the "morbidity rate of large-bowel cancer" and "polymorphism address" are recorded in memory section A10 in association with a predetermined "Gno."

In step D7 (SD7), "Gno." and "polymorphism address" recorded in memory section A10 are transmitted to personal computer 3 and instruction information instructing submission of a "polymorphism pattern" corresponding to the transmitted "polymorphism address" is transmitted to personal computer 3. At this time, the submission of additional information such as that concerning anamnesis and characteristics may be optionally instructed depending on the types of request information.

In step D8 (SD8), "Gno.," "polymorphism address," and instruction information transmitted from shared computer 2, are received. The received "Gno." and "polymorphism address" are recorded in memory section 26.

In step D9 (SD9), the received polymorphism address is transmitted to computer W used for providing flag information via communication network 1 in order to evaluate whether or not the "polymorphism address" received in step D8 has flag information provided thereon. When the databases shown in FIG. 13 are independently constructed with different settings for each "Gno.," "Gno." is transmitted together with polymorphism addresses in step D9.

In step D10 (SD10), computer W used for providing flag information receives the polymorphism address transmitted from personal computer 3, and accesses the database shown in FIG. 13 to inspect whether or not the received polymorphism address has flag information provided thereon. Specifically, computer W used for providing flag information searches for a polymorphism address that matches the received polymorphism address in the database shown in FIG. 13. When the received polymorphism address has flag information provided thereon, for example, such flag information is associated with the received polymorphism address.

In step D11 (SD11), the search result attained in step D10 is transmitted from computer W for providing flag information to personal computer 3. The flag information may be associated with the polymorphism address received in step D10 and transmitted as the search result. Information that indicates whether or not some of the polymorphism addresses received in step D10 have flag information provided thereon, i.e., whether or not the instruction information contains a polymorphism address having flag information provided thereon, may be transmitted as the search result. When some of the polymorphism addresses received in step D10 have flag information provided thereon, information indicating that the instruction information contains a polymorphism address having flag information provided thereon and a polymorphism address having flag information provided thereon may be transmitted as the search result.

When flag information is provided on a combination of a plurality of polymorphism addresses in the database as shown in FIG. 13 and all the polymorphism addresses constituting such combination are contained in the polymorphism addresses received in step D10, it is evaluated that "instruction information contains a polymorphism address having flag information provided thereon." When at least one of the polymorphism addresses constituting the combination is not contained in the polymorphism addresses received in step D10, it is evaluated that "instruction information does not contain a polymorphism address having flag information provided thereon."

In step D12 (SD12), personal computer 3 receives the search result transmitted from computer W used for providing flag information and confirms the search result. Thus, whether or not the polymorphism address contained in the instruction information has flag information provided thereon is evaluated. When a plurality of polymorphism addresses are received in step D8, whether or not all the polymorphism addresses have flag information provided thereon is evaluated. In step D12, when the polymorphism address contained in the instruction information has flag information provided thereon, a "yes" evaluation is made. When the polymorphism address contained in the instruction information does not have flag information provided thereon, a "no" evaluation is made. When a "yes" evaluation is made in step D12, the procedure is advanced to step D13 (SD13). In contrast, when a "no" evaluation is made in step D12, the procedure is advanced to step D14 (SD14).

When a plurality of polymorphism addresses are received in step D8, either of the following evaluation may be made in step D12. A "no" evaluation may be made when none of the polymorphism addresses have flag information provided thereon (evaluation 1). Alternatively, a "yes" evaluation is selectively made concerning the polymorphism address having flag information provided thereon, and a "no" evaluation is made concerning the polymorphism address having no flag information provided thereon, among a plurality of polymorphism addresses (evaluation 2).

When a plurality of polymorphism addresses are received in step D8, evaluation 1 is made in step D12, and at least one of the plurality of received polymorphism addresses has flag information provided thereon, a "yes" evaluation is made and the procedure is advanced to step D13. In such a case, the procedure is advanced to step D14 only when none of the received polymorphism address have flag information provided thereon.

In contrast, when a plurality of polymorphism addresses are received in step D8 and evaluation 2 is made in step D12, a "yes" evaluation is made concerning a polymorphism address having flag information provided thereon among the plurality of received polymorphism addresses. A "no" evaluation is made concerning a polymorphism address having no flag information provided thereon among the plurality of received polymorphism addresses. A procedure concerning the polymorphism address that has received a "yes" evaluation is advanced to step D13, and a procedure concerning the polymorphism address that has received a "no" evaluation is selectively advanced to step D14.

In step D13, notification of refusal of exhibition of polymorphism addresses contained in the instruction information is given to shared computer 2. When evaluation 1 is made in step D12, exhibition of polymorphism patterns corresponding to any polymorphism address is refused and notification of cancellation of the use of the present system is given to shared computer 2 in step D13. When evaluation 2 is made in step D12, exhibition of the polymorphism pattern corresponding to the polymorphism address having flag information provided thereon is refused in step D13, and notification of continuation of the use of the present system is given.

In step D14, genome-related information recording medium 24 is accessed in accordance with processing program 27, data II is searched, a polymorphism pattern in the polymorphism address having no flag information provided thereon is read out, and the polymorphism address is then recorded in memory section 26 in association with the polymorphism pattern. When evaluation 2 is made in step D12, polymorphism patterns are read out and recorded concerning only the polymorphism addresses having no flag information provided thereon among the plurality of received polymorphism addresses in step D14.

In step D14, whether the "Gno." contained in the instruction information is correct or not is preferably confirmed by accessing data I. In step D14, additional information recorded in data III, data IV, and data V is read out simultaneously with the polymorphism pattern and may be optionally recorded in memory section 26.

In step D15 (SD15), the temporarily-recorded polymorphism pattern associated with the polymorphism address and the optionally-recorded additional information in memory section 26 are output to shared computer 2 together with "Gno." through communication network 1. In step D16 (SD16), shared computer 2 receives the polymorphism pattern associated with the polymorphism address and the optionally-recorded additional information, and the received polymorphism pattern is recorded in memory section A10 in association with the polymorphism address.

In this embodiment, shared computer 2 transmits instruction information for exhibition of the "polymorphism pattern" in step D7, and personal computer 3 transmits the polymorphism address to the computer used for providing flag information to evaluate whether or not the polymorphism address contained in the instruction information has flag information provided thereon in step D9. The system, however, may not transmit the instruction information in step D7. In such a case, personal computer 3 searches for data II in step D9 based on the polymorphism address received in step D8, and transmits the received polymorphism address to the computer used for providing flag information to evaluate whether or not the received polymorphism address has flag information provided thereon in accordance with processing program 27.

In step D17 (SD17), main DB 14 is accessed to search information matching with the received polymorphism address and polymorphism patterns. More specifically, a plurality of polymorphism patterns are recorded in main DB 14 for one polymorphism address. Thus, which polymorphism pattern in main DB 14 matches with the received polymorphism address and the polymorphism pattern thereof is searched.

In step D18 (SD18), the morbidity rate of large-bowel cancer (semantic information) which is associated with the polymorphism pattern matching the received polymorphism pattern is read out in accordance with processing program 13. Specifically, in step D18, the morbidity rate of large-bowel cancer of a requester can be read out in accordance with the polymorphism address and polymorphism pattern submitted by the requester. The read-out morbidity rate is stored in memory section A10 in association with the requester's "Gno" and "polymorphism address," and "polymorphism pattern." At this time, the morbidity rate of large-bowel cancer may be corrected in accordance with additional information and then stored. Alternatively, other information obtained from additional information may be stored in association with the requester's "Gno."

When some of the polymorphism addresses and polymorphism patterns among the polymorphism addresses contained in the instruction information are received in step D16, a morbidity rate can be read out with the use of some of the received polymorphism addresses and polymorphism patterns in step D18.

Subsequently, in step D19 (SD19), the requester's "Gno." and morbidity rate, which are stored in memory section A10, are transmitted as semantic information to personal computer 3 through communication network 1. Personal computer 3 receives the requester's "Gno." and morbidity rate (semantic information) in step D20 (SD20). The received semantic information is recorded in memory section 26.

In step D21 (SD21), the morbidity rate of large-bowel cancer is displayed on display device 22 based on semantic information recorded in memory section 26 in accordance with processing program 27. Instead of steps D19 to D21, shared computer 2 can read out (prepare) a screen that displays semantic information in accordance with processing program 13, and display it on display device 22 of personal computer 3 through communication network 1. Also in this case, semantic information is considered to be transmitted from shared computer 2 to personal computer 3. As a result, the requester can obtain the morbidity rate of large-bowel cancer using genome-related information 28 recorded on genome-related information recording medium 24.

When "information associated with semantic information" is further drawn out from "semantic information" that has been read out in step D18, "semantic information" and "information associated with the semantic information" are transmitted in association with the polymorphism address in step D19, and they are received in step D20, and "semantic information" and "information associated with the semantic information" are displayed in step D21

In this system, in case that information concerning the provision of "functional foods that prevent large-bowel cancer" is further received in step D3 as requested information in addition to "the morbidity rate of large-bowel cancer" requested by the requester when, for example, the morbidity rate exceeds a given standard, the requested functional foods can be provided together with information concerning the morbidity rate of large-bowel cancer of the requester when the morbidity rate exceeds a given standard.

Up to steps D3 to D7 and step D16 in shared computer 2 may be carried out with an organization different from that of steps D16 to D19. In such a case, steps that are carried out in shared computer 2 are divided into two parts.

A polymorphism pattern may or may not be encrypted in this system.

As mentioned above, utilization of computer W used for providing flag information comprising a database having flag information recorded thereon and genome-related information recording medium 24, which has individuals' polymorphism patterns in association with polymorphism addresses recorded thereon, enables individuals to use semantic information recorded in main DB 14 through the polymorphism addresses in this system. An individual utilizing this system does not have to record semantic information on a genome-related information recording medium 24. Instead, the individual can obtain various types of semantic information simply by possessing genome-related information 28 having a polymorphism pattern related to the polymorphism address.

In the present system, by accessing computer W used for providing flag information prior to transmitting the polymorphism addresses and the polymorphism patterns to shared computer 2 via communication network 1, whether or not the polymorphism address to be transmitted has flag information provided thereon can be evaluated. Thus, leakage of polymorphism addresses and polymorphism patterns that should not be transmitted via communication network 1 can be prevented with the present system.

According to the present system, flag information is not necessarily recorded on genome-related information recording medium 24 because of the use of the flag information recorded in the database of the computer W used for providing flag information. If the newest flag information is updated on the computer W used for providing flag information side, for example, the requester can utilize the present system based on the newest flag information without the necessity of updating genome-related information recording medium 24.

In the present system, transmission of polymorphism addresses and polymorphism patterns can be regulated in accordance with a type of shared computer 2 (including a type of business and the presence or absence of public authorization) by setting 3 or more gradable values as flag information. In this case, personal computer 3 preferably transmits information concerning shared computer 2, for example, the rate that has been previously set for shared computer 2 or the name of shared computer 2, together with the "polymorphism address" in step D9. This enables the computer W used for providing flag information to search for the flag information in accordance with, for example, the rate or name of shared computer 2 from a database in step D10 (SD10). This system enables evaluation concerning adequacy of transmission of polymorphism addresses and polymorphism patterns for every shared computer 2 as a destination. Thus, inadequate leakage of polymorphism addresses and polymorphism patterns can be prevented.

Figure 16:
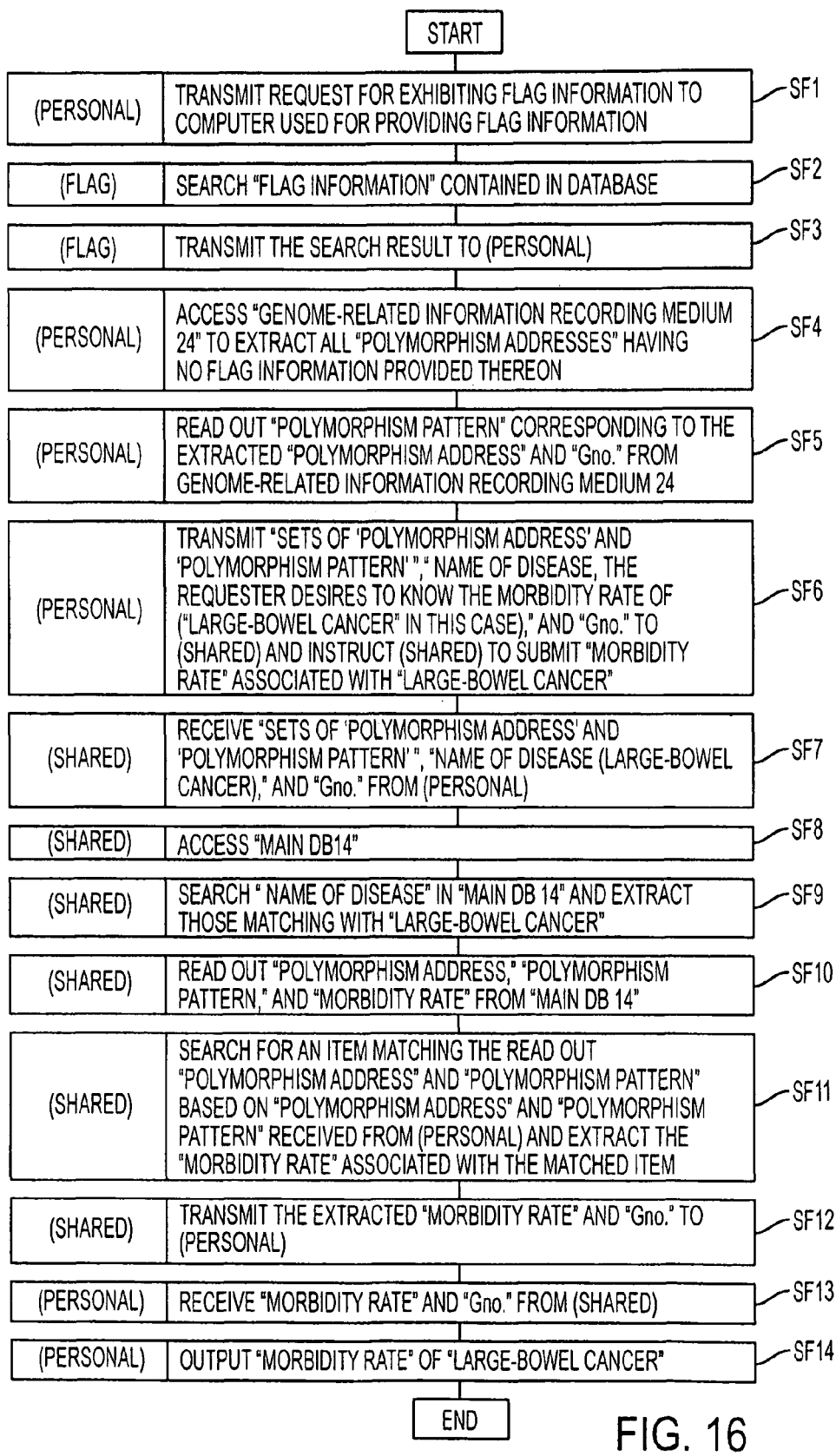
FIG. 16 is a flow chart showing another process in a shared computer, a personal computer and a computer used for providing flag information in the system according to the second embodiment.

In the system for processing information, processing program 13 recorded in storage 7 of shared computer 2 and processing program 27 recorded in storage 23 of personal computer 3 may process information in accordance with, for example, the flow chart shown in FIG. 16. Also in the flow chart shown in FIG. 11, a step described as "(shared)" refers to processing in shared computer 2, a step described as "(personal)" refers to processing in personal computer 3, and a step described as "(flag)" refer to processes in computer W used for providing flag information.

When utilizing the system, the requester first starts processing program 27 recorded in storage 23 and requests the computer W used for providing flag information to exhibit flag information in step F1 (SF1) in accordance with processing program 27. For example, when the computer W used for providing flag information comprises databases shown in FIG. 13 for each Gno., a request for exhibition of flag information and "Gno." are transmitted from personal computer 3.

In step F1, reading apparatus 25 may be driven to access genome-related information recording medium 24, and all the "polymorphism addresses" recorded as data II may be transmitted to computer W used for providing flag information to request exhibition of flag information concerning the transmitted polymorphism address.

In step F2 (SF2), computer W used for providing flag information receives a request for exhibition of flag information and searches for flag information contained in the database. Specifically, when computer W used for providing flag information comprises databases for each "Gno.," flag information contained in the database, which matches the received "Gno.," is searched.

In step F2, when a request for exhibition of flag information is received together with the polymorphism address, a database is searched based on the received polymorphism address, and flag information associated therewith is searched.

In step F3 (SF3), the search result attained in step F2 is transmitted from computer W for providing flag information to personal computer 3. Specifically, computer W for providing flag information transmits the polymorphism addresses in association with flag information contained in the database to personal computer 3.

In step F2, when a request for exhibition of flag information is received together with the polymorphism address, flag information is associated with the received polymorphism address and then transmitted to personal computer 3.

In step F4 (SF4), personal computer 3 receives the search result transmitted from computer W used for providing flag information and confirms the search result. Thus, a polymorphism address having no flag information provided thereon can be extracted from among all the polymorphism addresses recorded on genome-related information recording medium 24. The polymorphism address having no flag information provided thereon is stored in memory section 26.

Subsequently, the polymorphism address extracted in step F4, a polymorphism pattern corresponding thereto, and "Gno." are read out with the use of reading apparatus 25 in step F5 (SF5). The read-out "Gno.," "polymorphism address," and "polymorphism pattern" are stored in memory section 26.

In step F6 (SF6), based on a screen image displayed in accordance with processing program 27 on display device 22, information which the requester wishes to receive, for example the "morbidity rate of large-bowel cancer" (request information), is input to personal computer 3. At the same time, the "morbidity rate of large-bowel cancer" and "Gno.," "polymorphism address," and "polymorphism pattern" recorded in memory section 26 are transmitted to shared computer 2 from personal computer 3 through communication network 1.

In step F7 (SF7), shared computer 2 receives "morbidity rate of large-bowel cancer," "Gno.," "polymorphism address," and "polymorphism pattern." The received "morbidity rate of large-bowel cancer" is recorded as request information in memory section A10 and "Gno.," "polymorphism address" and "polymorphism pattern" are also stored in memory section A10. Shared computer 2 starts processing program 13 upon reception of the request information and, in step F8 (SF8), accesses main DB 14 in accordance with processing program 13.

In step F9 (SF9), in accordance with processing program 13, "classification (name of disease)" recorded in main DB 14 is searched and classification matching with the requested "morbidity rate of large-bowel cancer" (large-bowel cancer) is extracted.

In step F10 (SF10), main DB 14 is accessed to read out the "polymorphism address" classified as "large-bowel cancer," all the "polymorphism patterns" associated with the polymorphism address, and the "morbidity rate" in all the polymorphism patterns in accordance with processing program 13. The read-out "polymorphism address," "polymorphism pattern," and "morbidity rate" are stored in memory section A10.

In step F11 (SF11), the data stored in memory section A10 in step F10 is searched based on the "polymorphism address" and the "polymorphism pattern" received in step F7, and a morbidity rate associated with polymorphism pattern matching with the received "polymorphism pattern" is extracted from memory section A10.

In step F12 (SF12), the result of step F11, that is, the morbidity rate extracted according to which polymorphism pattern in main DB 14 matches with the polymorphism pattern contained in the received information in step F7, is transmitted to personal computer 3 through communication network 1. In this case, shared computer 2 transmits the extracted morbidity rate together with the requester's "Gno."

In step F13 (SF13), the "Gno." and "morbidity rate (semantic information)" transmitted from shared computer 2 is received. The received "Gno." and "morbidity rate" are recorded in memory section 26. At this time, data I recorded on genome-related information recording medium 24 is accessed and whether the received "Gno." is correct or not can be confirmed.

In step F14 (SF14), in accordance with processing program 27, the morbidity rate of large-bowel cancer is displayed on display device 22 based on semantic information recorded in memory section 26. Instead of steps F12 to F14, shared computer 2 can read out (prepare) a screen that displays semantic information in accordance with processing program 13, and display it on display device 22 of personal computer 3 through communication network 1. Also in this case, semantic information is considered to be transmitted from shared computer 2 to personal computer 3. This enables the requester to obtain the morbidity rate of large-bowel cancer using genome-related information 28 recorded on genome-related information recording medium 24.

More particularly, in accordance with the process of the flow chart shown in FIG. 16, all the polymorphism addresses having no flag information provided thereon and polymorphism patterns are inputted to shared computer 2 and semantic information to be provided to the requester is obtained in shared computer 2. In accordance with the process of the flow chart shown in FIG. 16, even with a relatively small number of times of reception/transmission of information between personal computer 3 and shared computer 2, the requester can obtain semantic information. Even if the information processing capacity of personal computer 3 is relatively low, therefore, the desired semantic information can be adequately provided in accordance with the process of the flow chart shown in FIG. 16. In addition, the requester can obtain semantic information in a very simple manner.

Further, when the present system is utilized in accordance with the process of the flow chart shown in FIG. 16, leakage of polymorphism addresses and polymorphism patterns that should not be transmitted via communication network 1 can be prevented because of the use of the polymorphism pattern of the polymorphism address on which no flag information has been provided.

According to the present system, flag information is not necessarily recorded on genome-related information recording medium 24 in accordance with the process of the flow chart shown in FIG. 16 because of the use of the flag information recorded in the database of the computer W used for providing flag information. If the newest flag information is updated on the computer W used for providing flag information side, for example, the requester can utilize the present system based on the newest flag information without the necessity of updating genome-related information recording medium 24.

In the present system, transmission of polymorphism addresses and polymorphism patterns can be regulated in accordance with a type of shared computer 2 (including a type of business and the presence or absence of public authorization) by setting 3 or more gradable values as flag information. In this case, personal computer 3 preferably transmits information concerning shared computer 2, for example, the grade that has been previously set for shared computer 2 or the name of shared computer 2, together with a "request for exhibition of flag information" in step F1. This enables the computer W used for providing flag information to search for the flag information in accordance with the grade or name of shared computer 2 from a database in step F2. Thus, the present system also enables evaluation concerning adequacy of transmission of polymorphism addresses and polymorphism patterns for every shared computer 2 as a destination. Thus, inadequate leakage of polymorphism addresses and polymorphism patterns can be prevented.

In the system for processing information, a recording medium prepared by removing information contained as data II from a genome-related information recording medium; that is, a recording medium having only data I and additionally data III to V, may be used. In this case, information contained as data II is recorded in an external database (genome-related information recording medium) connected to personal computer 3 via communication network 1. In such a system, for example, the external database is accessed via communication network 1 to read out the polymorphism pattern of the polymorphism address having no flag information provided thereon, and the polymorphism pattern can be recorded in association with the polymorphism address in memory section 26 in step D14 of the flow charts shown in FIGS. 14 and 15. Alternatively, for example, the external database is accessed via communication network 1 to read out the polymorphism patterns of all the polymorphism addresses having no flag information provided thereon, and the polymorphism pattern can be recorded in association with the polymorphism address in memory section 26 in step F4 of the flow chart shown in FIG. 16. As shown in the processes of the flow charts shown in FIGS. 14 and 15, and that of the flow chart shown in FIG. 16, the requester can obtain semantic information via such system.

The system for processing information may be equipped with genome-related information recording medium 24 connected to personal computer 3 via communication network 1 instead of the requester has genome-related information recording medium 24 or the recording medium prepared by removing information contained in data II from such genome-related information recording medium. In such a system, the requester can access genome-related information recording medium 24 through communication network 1 to download information such as "polymorphism addresses" and "polymorphism patterns" recorded on genome-related information recording medium 24 into personal computer 3. In this case, genome-related information recording medium 24 may comprise genome-related information of a plurality of individuals (each "Gno.") recorded thereon.

In addition, the present invention is not limited to the above-mentioned construction, i.e., shared computer 2 comprising main DB 14. For example, the present invention is applicable to a system for processing information equipped with main DB 14 connected to shared computer 2 via communication network 1. In this case, shared computer 2 accesses main DB 14 through communication network 1 in a manner as shown in the flow charts shown in FIGS. 14 and 15 and the flow chart shown in FIG. 16. In such a case, the requester can also obtain desired semantic information in accordance with the processes of the flow charts shown in FIGS. 14 and 15 or that of the flow chart shown in FIG. 16 according to the system for processing information.

More specifically, shared computer 2 can access a plurality of main DBs 14 owned by different organizations or groups through communication network 1 and can utilize semantic information contained in such plurality of main DBs 14, thereby providing information to the requester. In the system for processing information, shared computer 2 accesses various main DBs 14 containing information concerning the morbidity rate of large-bowel cancer as semantic information in step D4 as shown in the flow charts shown in FIGS. 14 and 15 or in step F8 as shown in the flow chart shown in FIG. 16. According to the system for processing information, therefore, the requester can obtain information concerning the morbidity rate of large-bowel cancer from information contained in a plurality of main DBs 14.

In this system, shared computer 2 may transmit at least the requested information received from personal computer 3 to a so-called agent and obtain semantic information ("morbidity rate of large-bowel cancer" in this embodiment) through the agent as shown in the processes of the flow charts shown in FIGS. 14 and 15 or that of the flow chart shown in FIG. 16.

All publications, patents, and patent applications cited herein are incorporated herein by reference in their entirety.

INDUSTRIAL APPLICABILITY

As is apparent from the foregoing description, the present invention can provide a highly safe system for providing information that can provide useful semantic information for an individual via effective utilization of differences in nucleotide sequence information among individuals and that can certainly prevent unfavorable leakage of nucleotide sequence information.

The invention claimed is:

1. A computer-implemented method for processing information on a nucleotide sequence comprising the steps of:
   transmitting, under control of a first processor, request information on a provision of an object or service for an individual to a second processor via a communication network;
   receiving from the second processor, via the communication network, positional information representing a position in a nucleotide sequence corresponding to the request information transmitted in the above transmitting step, wherein the first processor is permitted to access a first memory area storing positional information and nucleotide sequence-related information regarding the individual;
   obtaining flag information associated with positional information and/or information concerning the flag information, wherein the flag information is for evaluating adequacy of transmission of nucleotide sequence-related information associated with positional information;
   determining, based on the obtained flag information or information concerning the flag information, whether or not nucleotide sequence-related information corresponding to the positional information received in the receiving step should be transmitted to the second processor; and
   if said nucleotide sequence-related information is determined to be transmitted, retrieving said nucleotide sequence-related information from the first memory area; and outputting the retrieved nucleotide sequence-related information to the second processor,
   or, if said nucleotide sequence-related information is determined not to be transmitted in the determining step, the method further comprises the steps of: canceling the processing; or outputting a notification of refusal to transmit said nucleotide sequence-related information to the second processor;
   wherein the above steps are conducted under the control of the first processor.

2. The method for processing information on a nucleotide sequence according to claim 1, wherein the positional information received in the receiving step is retrieved, based on a classification that matches with the request information, from a third memory area, in the second processor, storing classification information in association with positional information.

3. The method for processing information on a nucleotide sequence according to claim 1, wherein the flag information or information concerning the flag information obtained in the obtaining step corresponds to all of the pieces of positional information that are received in the receiving step.

4. The method for processing information on a nucleotide sequence according to claim 1, wherein the flag information or information concerning the flag information corresponds to a piece of positional information or a combination of a plurality of pieces of positional information.

5. An apparatus for processing information on a nucleotide sequence comprising:
   a transmitter/receiver for transmitting request information on a provision of an object or service for an individual to a second processor via a communication network, and receiving from the second processor, via the communication network, positional information representing a position in a nucleotide sequence corresponding to the request information transmitted, wherein the apparatus is permitted to access a first memory area storing positional information and nucleotide sequence-related information regarding the individual; and
   a controller for obtaining flag information associated with positional information and/or information concerning the flag information, wherein the flag information is for evaluating adequacy of transmission of nucleotide sequence-related information associated with positional information, and for determining, based on the obtained flag information or information concerning the flag information, whether or not nucleotide sequence-related information corresponding to the positional information received by the transmitter/receiver should be transmitted to the second processor, wherein, if the controller determines said nucleotide sequence-related information to be transmitted, the controller retrieves said nucleotide sequence-related information from the first memory area, and outputs the retrieved nucleotide sequence-related information to the second processor, or, if the controller determines said nucleotide sequence-related information not to be transmitted, the controller cancels the processing, or outputs a notification of refusal to transmit said nucleotide sequence-related information to the second processor.

6. The apparatus for processing information on a nucleotide sequence according to claim 5, wherein the positional information received by the transmitter/receiver is retrieved, based on a classification that matches with the request information, from a third memory area in the second processor, storing classification information in association with positional information.

7. The apparatus for processing information on a nucleotide sequence according to claim 5, wherein the controller obtains flag information or information concerning the flag information corresponding to all of the pieces of positional information that are received by the transmitter/receiver.

8. The apparatus for processing information on a nucleotide sequence according to claim 5, wherein the flag information or information concerning the flag information corresponds to a piece of positional information or a combination of a plurality of pieces of positional information.

* * * * *